(12) United States Patent
Bangera et al.

(10) Patent No.: US 10,271,591 B2
(45) Date of Patent: Apr. 30, 2019

(54) PROTECTIVE GARMENT SYSTEMS FOR PROTECTING AN INDIVIDUAL AND METHODS OF USING THE SAME

(71) Applicant: Elwha LLC, Bellevue, WA (US)

(72) Inventors: Mahalaxmi Gita Bangera, Renton, WA (US); Jesse R. Cheatham, III, Seattle, WA (US); Roderick A. Hyde, Redmond, WA (US); Muriel Y. Ishikawa, Livermore, CA (US); Jordin T. Kare, San Jose, CA (US); Eric C. Leuthardt, St. Louis, MO (US); Elizabeth A. Sweeney, Seattle, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 15 days.

(21) Appl. No.: 15/223,277

(22) Filed: Jul. 29, 2016

(65) Prior Publication Data

US 2018/0027894 A1 Feb. 1, 2018

(51) Int. Cl.
| | | |
|---|---|---|
| *A41D 13/01* | (2006.01) | |
| *A41D 13/018* | (2006.01) | |
| *A63B 71/08* | (2006.01) | |
| *A41D 31/00* | (2019.01) | |
| *A41D 1/00* | (2018.01) | |
| *A61B 5/00* | (2006.01) | |

(52) U.S. Cl.
CPC ........... *A41D 13/018* (2013.01); *A41D 1/002* (2013.01); *A41D 31/005* (2013.01); *A63B 71/081* (2013.01); *A41D 2600/10* (2013.01); *A41D 2600/20* (2013.01); *A61B 5/0053* (2013.01); *A63B 2220/40* (2013.01); *A63B 2220/53* (2013.01); *A63B 2220/56* (2013.01)

(58) Field of Classification Search
CPC ................ A41D 13/018; A41D 13/015; A41D 2600/10; A41D 2600/20; A41D 13/00; A41D 13/005; A41D 1/00; A41D 1/002; A63B 71/081; A63B 2220/53; A63B 2220/56
USPC ........................................................... 2/455
See application file for complete search history.

(56) References Cited

U.S. PATENT DOCUMENTS

| | | | | |
|---|---|---|---|---|
| 2,028,060 | A * | 1/1936 | Eskell .................... | A01G 13/10 114/219 |
| 4,637,074 | A | 1/1987 | Taheri | |
| 5,148,002 | A * | 9/1992 | Kuo ...................... | H01Q 1/273 219/211 |
| 5,218,954 | A | 6/1993 | van Bemmelen | |
| 5,580,086 | A * | 12/1996 | McAlister .............. | B60R 21/20 280/737 |
| 6,032,299 | A * | 3/2000 | Welsh ................... | A41D 13/018 2/456 |
| 6,485,446 | B1 * | 11/2002 | Brother ................. | A41D 13/06 2/455 |

(Continued)

FOREIGN PATENT DOCUMENTS

EP 2807937 A1 12/2014

*Primary Examiner* — Shaun R Hurley
*Assistant Examiner* — Bao-Thieu L Nguyen
(74) *Attorney, Agent, or Firm* — Dorsey & Whitney LLP

(57) ABSTRACT

Embodiments disclosed herein are directed to systems for automatically protecting an individual from injuries using one or more sensors, one or more rigid members, and one or more inflatable members associated therewith, and methods of using the same.

48 Claims, 14 Drawing Sheets

(56) References Cited

U.S. PATENT DOCUMENTS

| | | | | |
|---|---|---|---|---|
| 6,547,284 | B2* | 4/2003 | Rose | F16L 37/56 285/1 |
| 6,560,789 | B2* | 5/2003 | Whalen | A42B 3/121 2/413 |
| 6,589,891 | B1* | 7/2003 | Rast | A41D 13/0158 2/455 |
| 6,796,865 | B2* | 9/2004 | Raithel | A41D 13/002 2/455 |
| 7,063,676 | B2* | 6/2006 | Barak | A61F 5/012 601/149 |
| 7,329,230 | B2* | 2/2008 | Mazzarolo | A41D 13/0531 128/846 |
| 7,650,648 | B2* | 1/2010 | Roberts | A41B 9/00 2/195.8 |
| 8,162,861 | B2* | 4/2012 | Avitable | A61H 9/0078 601/151 |
| 8,474,067 | B2* | 7/2013 | Reimer | A41D 13/0531 2/467 |
| 8,758,282 | B2* | 6/2014 | Malhi | A61H 9/0092 601/149 |
| 8,961,733 | B2* | 2/2015 | Dodd | A41D 13/0153 156/290 |
| 9,271,537 | B2* | 3/2016 | Nelson | A42B 3/121 |
| 9,380,834 | B2* | 7/2016 | Rushbrook | A43B 23/16 |
| 2001/0023504 | A1* | 9/2001 | Yoon | A63B 69/26 2/455 |
| 2002/0092088 | A1 | 7/2002 | Duhamell | |
| 2002/0153009 | A1* | 10/2002 | Chornyj | A62B 7/02 128/201.27 |
| 2003/0188371 | A1 | 10/2003 | Duhammel et al. | |
| 2005/0067816 | A1 | 3/2005 | Buckman | |
| 2006/0218706 | A1 | 10/2006 | Mazzarolo et al. | |
| 2006/0267779 | A1 | 11/2006 | Ishikawa et al. | |
| 2007/0147272 | A1 | 6/2007 | Mazzarolo | |
| 2012/0073035 | A1 | 3/2012 | Mazzarolo et al. | |
| 2012/0131718 | A1 | 5/2012 | Uchida et al. | |
| 2013/0232674 | A1* | 9/2013 | Behrend | A41D 13/0002 2/455 |
| 2014/0026302 | A1 | 1/2014 | Mcqueer | |
| 2015/0128334 | A1 | 5/2015 | Mazzarolo et al. | |
| 2015/0164154 | A1* | 6/2015 | Bencini | A41D 13/0531 2/455 |
| 2015/0173431 | A1* | 6/2015 | Oliver | A41D 13/005 2/455 |
| 2015/0173433 | A1 | 6/2015 | Mazzarolo et al. | |
| 2015/0297973 | A1* | 10/2015 | Beers | A63B 71/12 2/461 |
| 2016/0183605 | A1* | 6/2016 | Leschinsky | A41D 13/0012 2/247 |
| 2016/0183607 | A1* | 6/2016 | Lopez Yunez | A41D 13/018 2/455 |
| 2016/0270472 | A1* | 9/2016 | Allen | A42B 3/0486 |
| 2016/0374886 | A1* | 12/2016 | Wyatt | A61N 1/36014 601/18 |
| 2017/0049164 | A1* | 2/2017 | Gruentzig | A42B 3/046 |
| 2017/0095396 | A1* | 4/2017 | Chase | A41D 1/00 |
| 2017/0224031 | A1* | 8/2017 | Raanan | A41D 13/018 |
| 2017/0360122 | A1* | 12/2017 | Chin | A41D 1/002 |

* cited by examiner

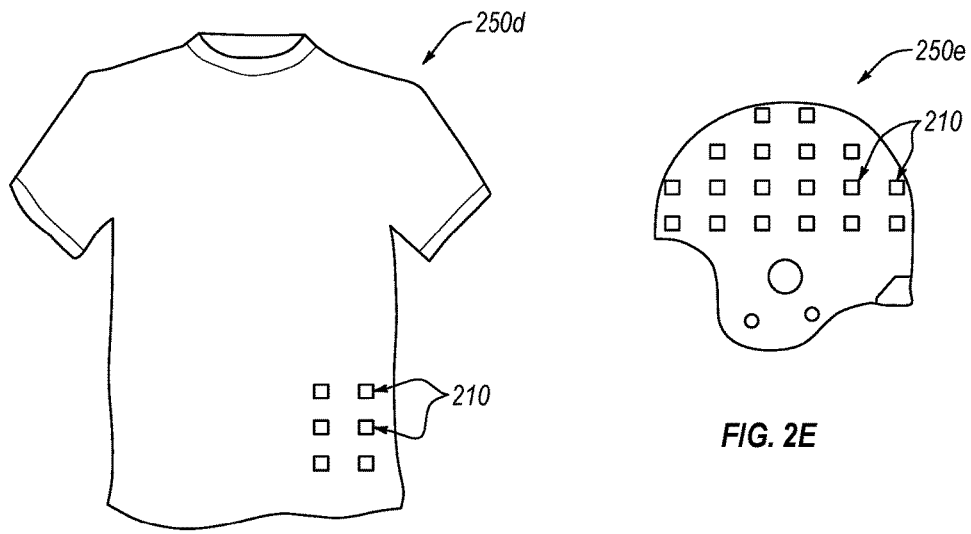
FIG. 2D
FIG. 2E
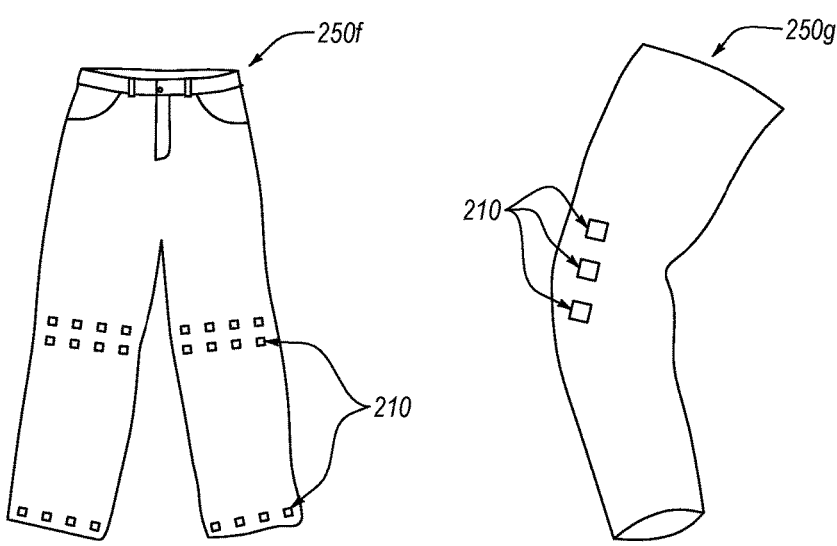
FIG. 2F
FIG. 2G

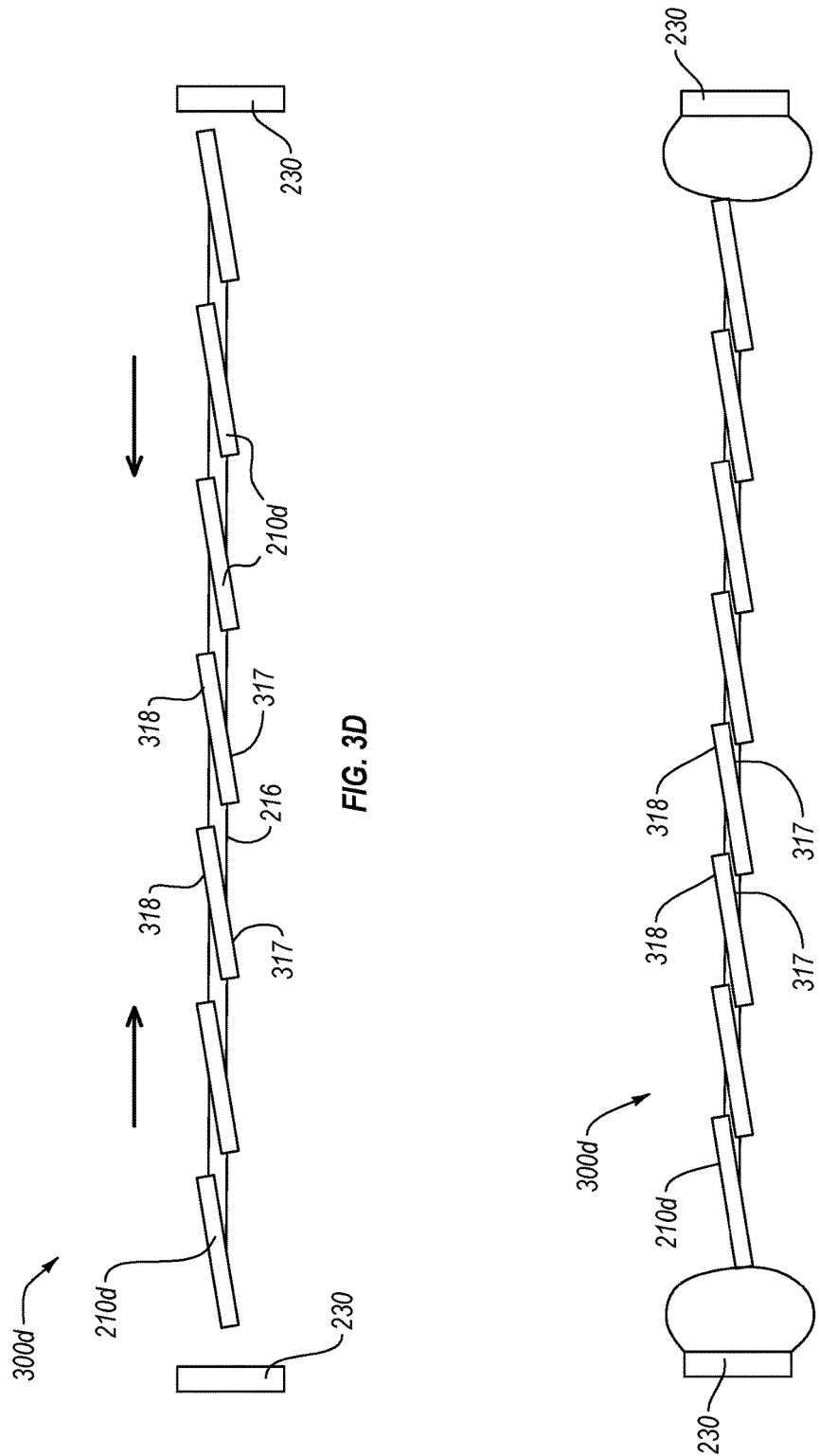

PROTECTIVE GARMENT SYSTEMS FOR PROTECTING AN INDIVIDUAL AND METHODS OF USING THE SAME

If an Application Data Sheet (ADS) has been filed on the filing date of this application, it is incorporated by reference herein. Any applications claimed on the ADS for priority under 35 U.S.C. § § 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

Priority Applications

None.

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

BACKGROUND

Impact injuries are sustained from impacts of objects against an individual and impact of the individual against objects. Impact injuries include blunt force traumas, punctures, concussion, broken bones, damaged joints, and other medical conditions. Equipment for prevention of impact injuries has existed for many centuries in many forms, including medieval armor and ancient Egyptian helmets.

Prevention of impact injuries has led to the development of modern safety equipment, such as hardhats, batting helmets, football pads, knee-braces, and body armor such as bullet proof vests, etc. Some safety equipment useful for preventing impact injuries is bulky, cumbersome, heavy, and can limit movement. For example, football pads can limit movement and tend to be bulky. Knee or other joint braces can unduly limit range of motion. Body armor tends to be bulky, heavy, and may limit range of motion in some cases.

SUMMARY

Embodiments disclosed herein are directed to protective garment systems and methods of using the same. In an embodiment, a protective garment system is disclosed. The protective garment system includes a plurality of rigid members. Each of the plurality of rigid members is coupled to at least one adjacent rigid member of the plurality of rigid members. The protective garment system further includes at least one fluid source and a plurality of inflatable members. Each of the plurality of inflatable members is operably coupled to the at least one fluid source and associated with at least one of the plurality of rigid members. The protective garment system also includes one or more sensors configured to sense at least one of a potential impact or an actual impact of the individual. The protective garment system additionally includes a controller operably coupled to the one or more sensors and the at least one fluid source.

In an embodiment, a method of protecting one or more body parts of an individual is disclosed. The method includes, with one or more sensors, sensing one or more of a potential impact or an actual impact against a protective garment worn by the individual. The protective garment includes a plurality of rigid members, with each of the plurality of rigid members coupled to at least one adjacent one of the plurality of rigid members. The garment further includes one or more inflatable members, with each of the one or more inflatable members operably coupled to at least one fluid source. The garment also includes the one or more sensors and a controller operably coupled to the one or more sensors and the at least one fluid source. The method includes with the controller, determining if a deployment condition is required based at least partially on sensing one or more of a potential impact or an actual impact. The method also includes, with the controller, controlling a change in volume of one or more of the plurality of inflatable members effective to move the one or more of the plurality of rigid members from a first position to a second position relative to at least another one of the plurality of rigid members.

Features from any of the disclosed embodiments can be used in combination with one another, without limitation. In addition, other features and advantages of the present disclosure will become apparent to those of ordinary skill in the art through consideration of the following detailed description and the accompanying drawings.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIGS. 2D-2G are schematics of garments that can include any of the protective members disclosed herein, according to different embodiments.

FIGS. 3D and 3DD are schematics of a plurality of rigid members of a protective garment system in a first state and a second state, respectively, according to an embodiment.

DETAILED DESCRIPTION

Figure 1:
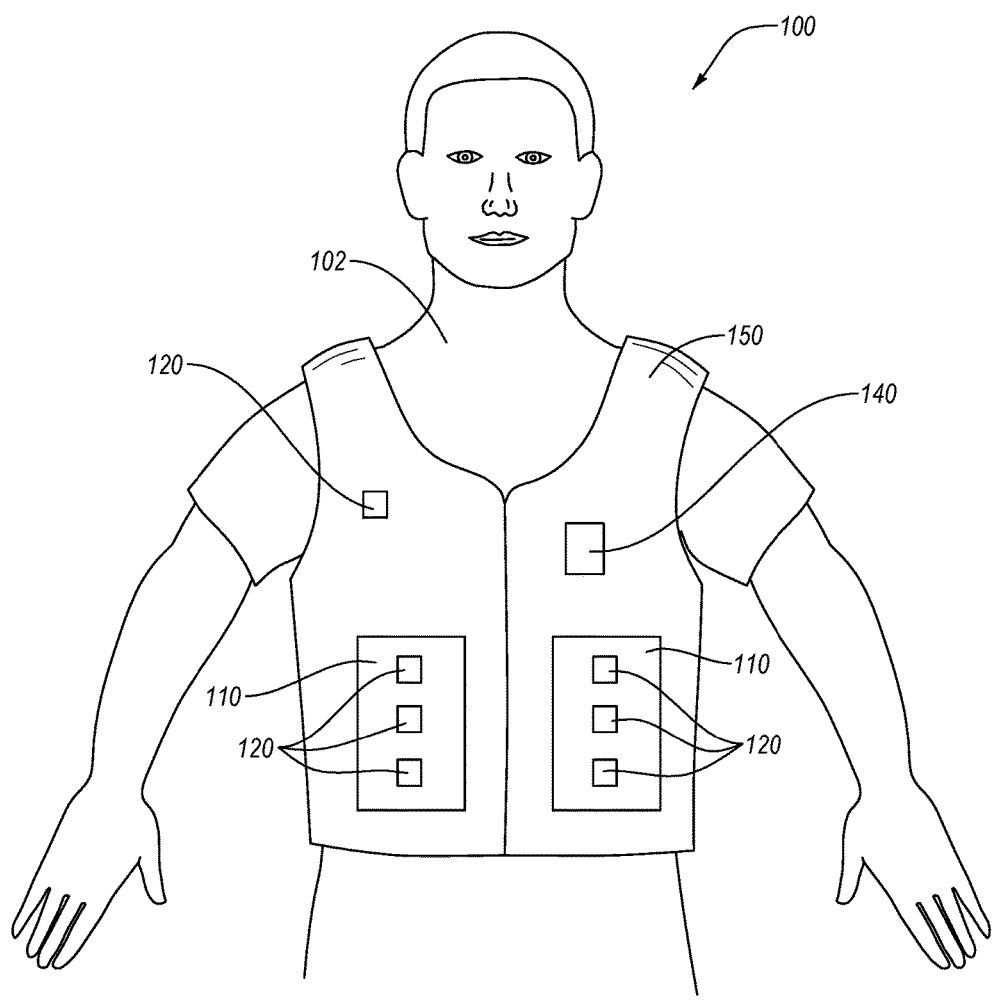
FIG. 1 is a schematic of a system for protecting an individual from injuries, according to an embodiment.

Embodiments disclosed herein relate to systems for automatically protecting an individual (e.g., human or non-human animal) from injuries using one or more sensors and one or more protective members, and methods of using the same. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

FIG. 1 is a schematic of a system 100 for protecting an individual 102 from injuries such as impacts, punctures wounds, concussion, etc., according to an embodiment. The system 100 includes one or more protective members 110, one or more sensors 120, and at least one controller 140. At least one of the one or more protective members 110, one or more sensors 120, or at least one controller 130 can be supported by a supportive member 150. The supportive member 150 can include a garment that may be worn by the individual 102. The one or more protective members 110 are configured to change from a first state to a second state responsive to direction from the at least one controller 140. In the first state, the protective members 110 can be configured to provide relative flexibility freedom of movement to a body part of the individual (e.g., leg, torso, etc.) or a portion of the supportive member 150 (e.g., sleeve, body panel, waist, abdominal region, etc.) adjacent thereto. In the second state, the protective members 110 can be configured to provide relative inflexibility or rigidity to one or more of the body part of the individual 102 and portion of the supportive member 150 adjacent thereto for enhanced protection of the individual 102 from injuries. In an embodiment, the first state can provide less relative rigidity than the second state. The relative rigidity of the second state may provide one or more of impact resistance, structural support, or force-dampening effects to a body part of the individual 102 or to the supportive member 150.

The one or more sensors 120 can sense at least one of a potential impact or an actual impact, as described in detail below. For example, the potential impact source or actual impact source can be another individual, another athlete (e.g., a football player), a projectile (e.g., a ball, falling debris), a surface (e.g., a road, a playing surface), etc. The sensed potential impact or actual impact can be relayed from the one or more sensors 120 to the controller 140, as described in detail below. The controller 140 is configured to selectively direct one or more of the protective members 110 to alter from the first state to the second state, vice versa, or some intermediate state therebetween, responsive to the sensed impact or potential impact, as described in detail below.

The protective members of the systems disclosed herein include one or more rigid members and one or more inflatable members. The volume of a fluid (e.g., one or more of a liquid or gas) in the one or more inflatable members can be controlled via the controller to cause the one or more inflatable members to inflate, deflate, or maintain a volume therein. The control of the inflatable members can cause the one or more rigid members to move in a desired direction, such as to one or more of interlock, form a pattern, unlock, or adjust a facial angle or other spatial relationship thereof relative to another rigid member. The controller can direct or control the inflatable members at least partially responsive to the one or more sensors sensing one or more of an actual impact, a potential impact, a radius of curvature of an impacting object, or a velocity (or other force) of the actual impact or potential impact.

Figure 2A:
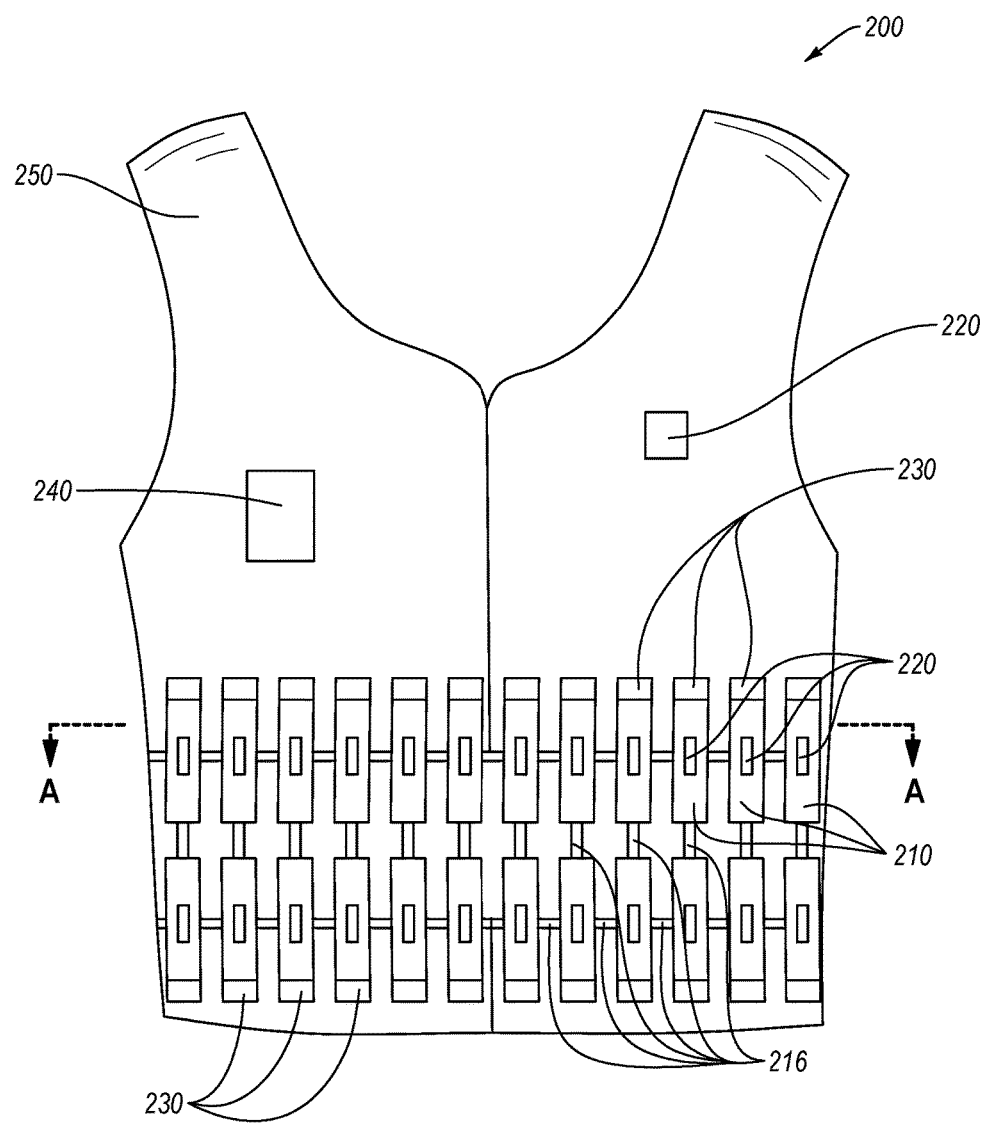
FIGS. 2A-2C are front views of protective garment systems, according to various embodiments.
Figure 2B:
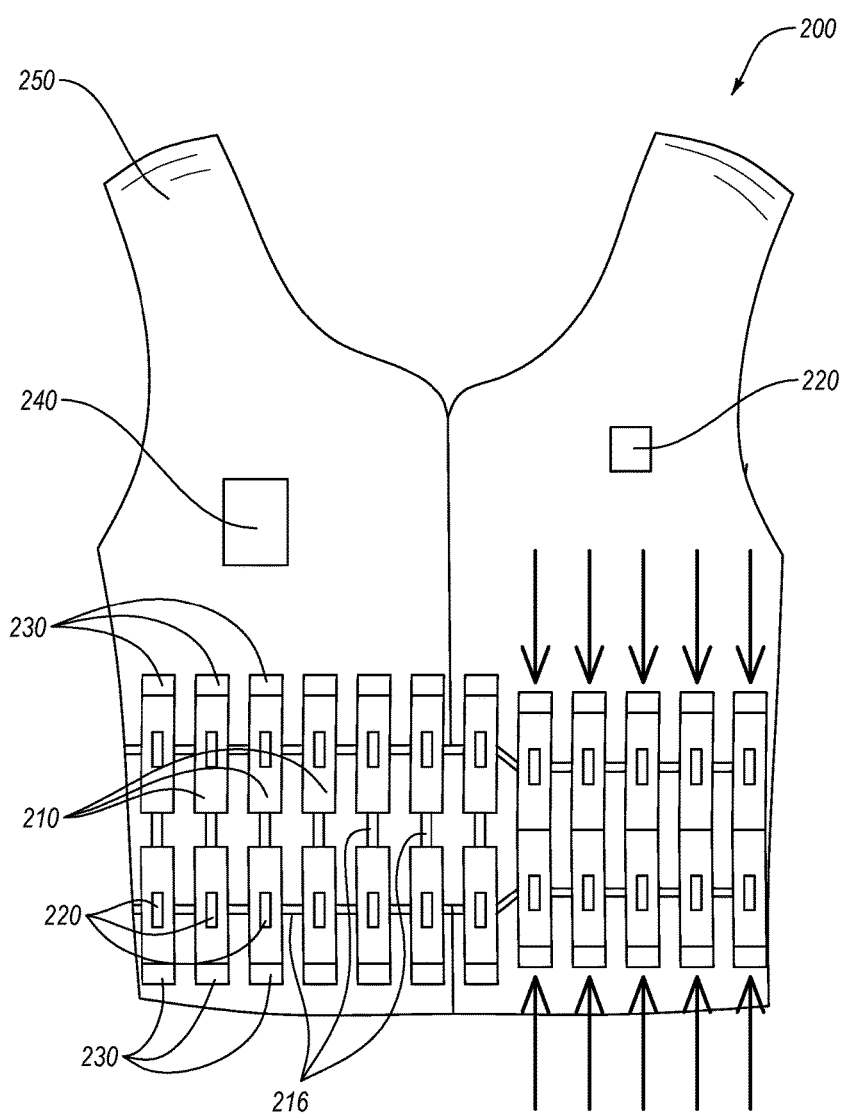

FIGS. 2A and 2B are front views of a protective garment system 200, according to an embodiment. The garment system 200 can protect an individual from one or more of impact, puncture wounds, concussion, or other trauma associated with one or more forces. The garment system 200 includes a plurality of rigid members 210, one or more sensors 220, one or more inflatable members 230, and a controller 240. The controller 240 is operably coupled to one or more of the plurality of rigid members 210, one or more sensors 220, or one or more inflatable members 230. The controller 240 is configured to receive sensor data indicative of at least one of a potential or an actual impact, and direct the one or more inflatable members 230 to alter an internal volume thereof. Inflation or deflation of the one or more inflatable members 230 can at least partially alter a spatial arrangement of the plurality of rigid members 210 by moving the rigid members 210 from a first state (e.g., first arrangement) to a second state or vice versa. The protective garment system 200 can include a supportive member 250. The supportive member 250 can support one or more of the plurality of rigid members 210, at least one of the one or more sensors 220, the one or more inflatable members 230, or the controller 240.

The plurality of rigid members 210 can include a plurality of plates, tiles, scales, panels, elongated members, or other bodies or shield segments designed to at least one of absorb, deflect, block or otherwise shield from impact forces. The plurality of rigid members 210 can include any material suitable for absorbing, deflecting, or blocking. In an embodiment, the plurality of rigid members 210 can include a foam, a metal or alloys (e.g., steel, titanium, aluminum, or alloys), a ceramic (e.g., one or more of boron carbide, silicon carbide, tungsten carbide, or aluminum oxide), a polymeric material (e.g., para-aramids such as Kevlar®; nylon; polyvinyl chloride; polyoxymethylene; acrylonitrile butadiene styrene; polyethylene, or any other plastic with similar impact resistance to the preceding), wood, graphene, carbon nanotubes, combinations or composites of any of the foregoing, or any other material suitable for shielding an individual from impact.

For example, the supportive member 250 can include athletic apparel or gear (e.g., football jersey, hockey girdle, etc.) and the plurality of rigid members 210 can be positioned on the supportive member 250 to at least partially protect an individual wearing the supportive member 250 from injuries that can occur during an athletic event. In another example, the supportive member 250 can include a garment, apparel, or gear that is worn during a potentially hazardous activity. The hazardous activity can include an activity that includes projectiles or other actual or potential impact sources. In particular, the supportive member 250 can be at least a portion of military apparel, policeman's uniform, fireman's uniform, first responder's uniform, construction worker's apparel, paintball apparel, motorcycle safety apparel, tactical gear, or other similar apparel. In some embodiments, the supportive member 250 can include an article of clothing or apparel. In some embodiments, the supportive member 250 can include protective gear (e.g., a rib guard, a helmet, or a hockey girdle). In some embodiments, the supportive member 250 can include supportive gear or apparel such as a brace or athletic supporter.

Figure 2C:
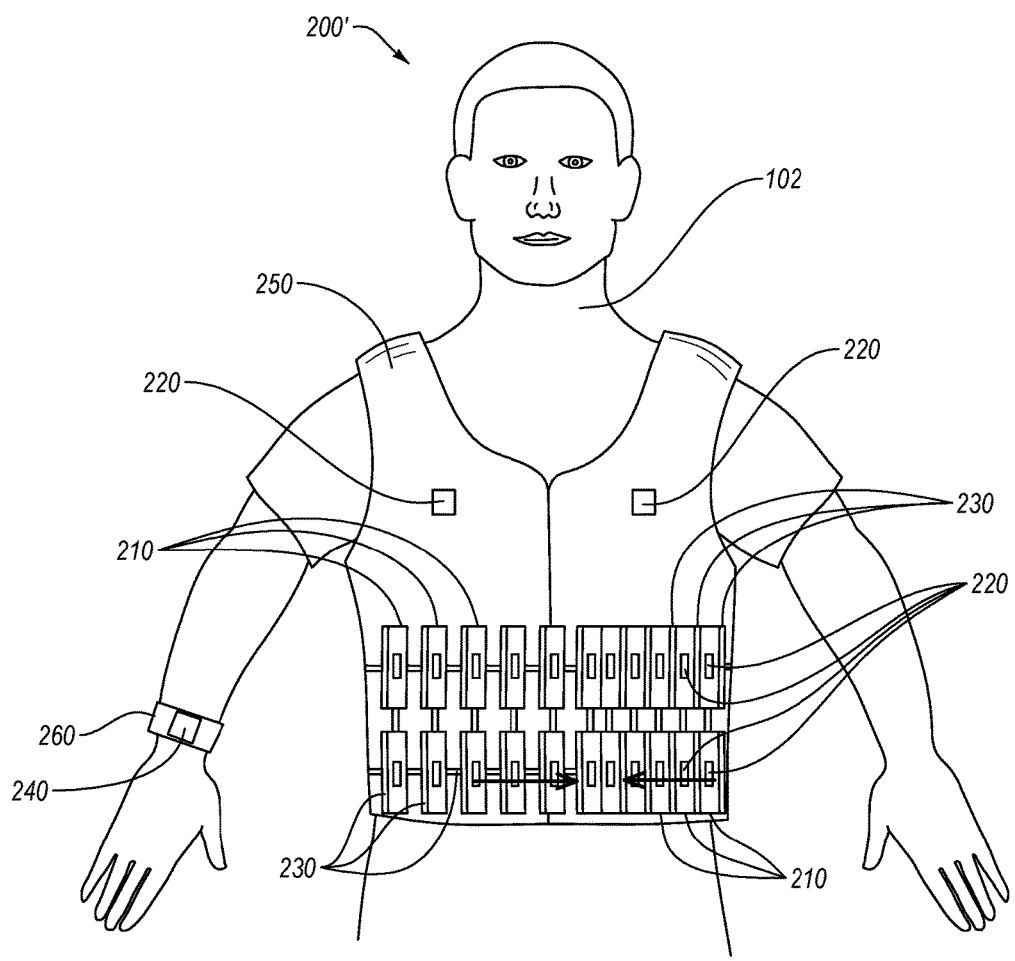

While each of the rigid members 210 shown in FIGS. 2A-2C are generally rectangular, each of the rigid members 210 can be configured in any shape (e.g., 2-dimensional shape) such as circular, semi-circular, elliptical, semi-elliptical, or polygonal (e.g., triangular, trapezoidal, square, octagonal, etc.). In some embodiments, a first plurality of rigid members 210 can include a first shape and at least a second plurality of rigid member 210 can include at least a second shape, where the first shape and second shape are any of the shapes disclosed herein. In some embodiments, at least some of the rigid members 210 may collectively form an array having a general shape, such as rectangular or any of the other shapes disclosed above. The plurality of rigid members 210 can have various dimensions. For example, the plurality of rigid members 210 can have a height or width of at least about 0.5 cm, such as about 0.5 cm to about 20 cm, about 1 cm to about 15 cm, about 2 cm to about 10 cm, or less than about 5 cm. The plurality of rigid members 210 can be at least about 1 mm thick, such as about 1 mm to about 2 cm, about 2 mm to about 1.5 cm, about 5 mm to about 1 cm, or less than about 2 cm. In an embodiment, the rigid members 210 can be shaped in a third dimension. For example, each of the plurality of rigid members 210 can be configured to substantially contour an anatomical feature of an individual. The plurality of rigid members can be molded or otherwise formed to conform to any body region (e.g., physiological features) of the individual, for example a specific individual, when in one or more of the first position, the second position, or an intermediate position therebetween. For example, each of the plurality of rigid members may be slightly arcuate or curved to contour to an arm, abdomen, or other body part. In an embodiment, each of the plurality of rigid members can be configured to collectively contour one or more anatomical features of the individual. In an embodiment, one or more of the plurality of rigid members can be configured to interlock or form a pattern upon a change from a first state to a second state.

The plurality of rigid members 210 can be disposed in a pattern or arrangement with respect to one or more adjacent rigid members of the plurality of rigid members 210. For example, as shown in FIG. 2A, each of the plurality of rigid members 210 can be arranged in a substantially linear or substantially parallel orientation with respect to one or more adjacent rigid members of the plurality of rigid members 210. In an embodiment, the plurality of rigid members 210 can be arranged in a configuration effective to at least partially interlock with one or more adjacent rigid members, at least partially overlap one or more adjacent rigid members, or at least partially form a pattern or array with one or more adjacent rigid members. Suitable patterns and arrangements of the rigid members are described in more detail below.

In an embodiment, each of the plurality of rigid members 210 can be coupled to at least one adjacent rigid member 210 via one or more linkages 216. The linkages 216 can be configured to change from a first linkage state to a second linkage state, or vice versa, responsive to a pressure exerted thereon from the one or more inflatable members 230. In an embodiment, the one or more linkages 216 are configured to maintain the one or more adjacent rigid members 210 in the first linkage state prior to a change in volume (e.g., inflation or deflation) of the one or more of the plurality of inflatable members 230 associated therewith. The one or more linkages 216 can include one or more of a bridging material (e.g., fabric tethers), a resilient material (e.g., neoprene, rubber, spring, etc.), or a fastener (e.g., clip, latch, snap-lock, etc.).

The bridging material can provide a linkage between adjacent rigid members 210. The resilient material can provide a resiliently deformable linkage between adjacent rigid members 210 that is sufficiently strong to hold the adjacent rigid members 210 in position and accommodate some movement therebetween. For example, the linkage 216 can include a spring that is resiliently deformable responsive to the increase of gas in the inflatable reservoir of the one or more of the plurality of inflatable members.

In an embodiment, fasteners can provide a mechanical connection or lock between adjacent rigid members 210 in a specific position or state. For example, the one or more linkages 216 can include a latch that is reversibly separable. Suitable latches can include one or more of a compression latch, a draw latch, or a hook latch, etc. In an embodiment, a latch can be configured as an opposing tooth pattern, a snap-lock design, hooks, or any other suitable latching relationship between one or more members of the latch. In an embodiment, the one or more linkages 216 can include a latch that is reversibly separable responsive to the increase or decrease of fluid in the inflatable reservoir of the one or more of the plurality of inflatable members. In an embodiment, the latch can be configured to be controlled (engaged or released) by the controller. In an embodiment, the one or more linkages 216 can include a both a resilient material and a fastener. For example, the one or more linkages can include neoprene strips and latches attached to adjacent surfaces of adjacent rigid members 210.

In an embodiment, the one or more linkages 216 (e.g., latch(es)) can separate or reconnect responsive to a change in volume (e.g., addition or depletion of a fluid in an inflatable reservoir) of the one or more of the plurality of inflatable members 230. In an embodiment, the one or more linkages 216 can remain in the first linkage state prior to a change in volume (e.g., inflation or deflation) of the one or more of the plurality of inflatable members 230. In an embodiment, the one or more linkages 216 (e.g., latch(es)) can remain in the second linkage state after change in volume (e.g., inflation or deflation) of the one or more of the plurality of inflatable members 230. In an embodiment, the linkages 216 in the second linkage state can hold the plurality of rigid members in a protective configuration (e.g., adjacent rigid members are closer to each other than in the first linkage state, overlap, or interlocked) on the individual. In an embodiment, the controller 240 can be configured to control the one or more inflatable members 230 or linkages (e.g., latches) effective to disconnect or reconnect the linkages.

As shown in FIGS. 2A-2C, the one or more linkages 216 are disposed on adjacent surfaces of adjacent rigid members of the plurality of rigid members 210. In an embodiment, one or more surfaces (e.g., sides or edges) of a rigid member of the plurality of rigid members 210 can have one or more linkages 216 disposed thereon, which linkages 216 can be further attached to one or more adjacent rigid members 210.

As shown in FIGS. 2A and 2B, the one or more linkages 216 can be configured to hold the plurality of rigid members 210 in a first state (FIG. 2A) prior to a change in volume of the inflatable members 230 and hold the plurality of rigid members 210 in a second state (FIG. 2B) after a change in volume of the inflatable members 230. The rigid members are longitudinally biased toward each other after the change in volume and the linkages 216 hold the adjacent ends of the plurality of rigid members 210 together.

The protective garment system 200 includes one or more sensors 220. The one or more sensors 220 can be disposed anywhere on the protective garment system 200, such as on one or more portions of the supportive member 250. Furthermore, in an embodiment, the one or more sensors 220 can be located remote from the supportive member 250, but in a suitable location for sensing at least of an actual or a potential impact of an individual, such as on a separate wearable device (e.g., a wristband).

In an embodiment, at least one of the one or more sensors 220 can be disposed proximate to (e.g., in contact with, over, or within 6 inches of) at least one of the plurality of rigid members 210, at least one of the plurality of inflatable members 230, or a specific region of the protective garment system 200. The one or more sensors 220 can sense at least one of actual or potential impacts (or forces indicative thereof) proximate to one or more specific regions of the protective garment system or specific rigid members of the plurality of rigid members 210. In an embodiment, the sensors 220 can sense the actual or potential impact in one or more specific regions of the protective garment system 200 and the rigid members in the one or more specific regions can be automatically moved by the controller 240 using the one or more inflatable members 230 in the one or more specific regions. The specific regions herein can be any size or include areas adjacent to one or more portions of any anatomical structure of the individual or corresponding portion of the protective garments system. In some embodiments, the specific regions can each include one rigid member 210 and one inflatable member 230 (e.g., in a pair or set), or can include a plurality of rigid members 210 and a plurality of inflatable member 230 (e.g., in pairs or sets). In an embodiment, the sensors 220 can sense the actual or potential impact in a specific region of the protective garment system 200 and all of the rigid members 210 in the specific region can be automatically moved by the controller 240 using the one or more inflatable members 230. As shown in FIGS. 2A-2C, in an embodiment, at least one of the rigid members 210 can include sensors 220 directly associated therewith, such as disposed thereon or there over.

In an embodiment, the one or more sensors 220 can include a sensor array disposed over substantially the entire supportive member 250. In an embodiment, at least one of the one or more sensors 220 can be disposed remotely (e.g., more than 6 inches away) from the plurality of rigid members 210. In an embodiment, at least one of the one or more sensors 220 can be disposed on the same portion of the supportive member 250 as the rigid members 210 but remotely therefrom, such as on a chest region while the plurality of rigid members 210 are disposed about a back, abdominal, or oblique region of the supportive member 250.

The one or more sensors 220 can be configured to sense at least one of a potential or an actual impact. For example, the one or more sensors 220 include one or more of accelerometers, proximity sensors, optical sensors, topography sensors, thermal sensors, force sensors, acoustic sensors, among others. For example, the potential impact source or actual impact source can be another individual, another athlete (e.g., a football player), a projectile (e.g., a ball, falling debris), a surface (e.g., a road, a playing surface), etc.

In an embodiment, the sensors 220 can include one or more accelerometers configured to sense the movement of the individual, the potential impact source, or the actual impact source. In an embodiment, the sensors 220 can include one or more proximity sensors configured to sense one or more characteristics of the individual, the potential impact source, or the actual impact source. The one or more proximity sensors can include an infrared sensor, sonar, a laser rangefinder, a micro-impulse radar, an inductive sensor, a capacitive sensor, a photoelectric sensor, an ultrasonic sensor, etc. In an embodiment, the sensors 220 can include one or more optical sensors configured to sense one or more characteristics of the individual, the potential impact source, or the actual impact source. The one or more optical sensors can include an active-pixel sensor, light-emitting diodes that are reversed biased, a transducer, etc. For example, the optical sensors can be configured to sense a geometry of the potential or actual impact source. In an embodiment, the sensors 220 can include one or more topography sensors configured to sense a radius of curvature of the potential impact source of the actual impact source. In an embodiment, the one or more sensors can include a thermal sensor configured to sense one or more characteristics of the individual, the potential impact source, or the actual impact source. In an embodiment, the sensors 220 can include a force sensor configured to sense one or more characteristics of the actual impact. The force sensor can include a pressure sensor, a transducer, a displacement sensor, etc. In an embodiment, the sensors 220 can include one or more acoustic sensors configured to sense one or more characteristics of the individual, the potential impact source, or the actual impact source. For example, example, an acoustic sensor can sense a hardness of an impact source. In an embodiment, the sensors 220 can include an inertia sensor (e.g., MEMS inertia sensor) configured to sense movement of the individual. In an embodiment, the sensors 220 can include a heart rate monitor configured to sense the heart rate of the individual. In an embodiment, the sensors 220 can include a moisture sensor configured to sense sweat, blood, other body fluids, or other fluids.

The one or more sensors 220 can be configured to sense one or more of direction of travel of at least a portion of the individual, velocity of at least a portion of the individual (e.g., direction specific, linear, rotational, or angular velocities), acceleration of at least a portion of the individual (e.g., direction specific, linear, rotational, and angular acceleration), deceleration of at least a portion of the individual, a pressure applied to a portion of the individual or sensors on the supportive member (e.g., protective garment) worn by the individual by an object (e.g., including direction or trajectory of the source of the pressure), a radius of curvature of the object contacting the protective garment system, a predicted force (e.g., tension, stress, strain, etc.) on a body part of the individual, or a direction of likely impact to at least one body part of the individual.

In an embodiment, each of the one or more sensors 210 can be configured to sense the same or different forces (e.g., aspects of an actual or potential impact). For example, in an embodiment, adjacent sensors 220 can be configured to sense different information, such as a force sensor adjacent to an accelerometer. In an embodiment, each of a plurality of adjacent sensors can be configured to sense the same information, such as pressure or force. In an embodiment, an additional remote sensor can be configured to sense different information, such as orientation, velocity, or position of the supportive member 250 or objects in the vicinity of the supportive member 250.

The protective garment system 200 includes one or more inflatable members 230. The plurality of inflatable members 230 can be configured to move one or more of the plurality of rigid members 210 from a first position to a second position relative to at least another one of the plurality of rigid members 210. Each of the plurality of inflatable members 230 can be associated with at least one of the plurality of rigid members 210. The plurality of inflatable members 230 can be disposed at least adjacent to (e.g., on, contacting, or proximate to) one or more of the plurality of rigid members 210.

In some embodiments, each of the plurality of inflatable members 230 includes at least one inflatable reservoir (FIG. 5C) capable holding or expelling a volume of a fluid. The inflatable reservoirs can be made of any suitable material for holding a fluid, such as one or more of a fabric (e.g., nylon, polyester, etc.), a polymer, or a foil. In some embodiments, the inflatable members 230 can include at least one fluid source (FIGS. 5B-5F) operably coupled to the inflatable reservoir, such as one or more chemical reactants configured to supply a gas upon reaction thereof. In an embodiment (FIG. 5D), the fluid source can be separate from, but operably coupled to, the inflatable reservoir of the inflatable members 230, such as a gas reservoir connected to the inflatable reservoir via a conduit. Responsive to increase in volume of the internal space of the inflatable reservoir, such as by increase in the volume of a fluid therein, the one or more inflatable members 230 are inflated (FIGS. 5B and 5C). The internal volume of the inflatable member 230 can be changed by addition of fluid such as a gas therein by the fluid source.

The plurality of inflatable members 230 can be positioned and configured to cause one or more of the rigid members 210 to move in a selected direction upon a change in volume of the inflatable reservoirs therein. In an embodiment, each of the plurality of inflatable members 230 is associated with (e.g., adjacent to, contacting, or secured to) one of the plurality of rigid members 210. In an embodiment, each of the plurality of inflatable members 230 is associated with at least two of the plurality of rigid members 210.

As shown in FIGS. 2A-2C, in an embodiment, the plurality of inflatable members 230 can be disposed at least adjacent to one or more first ends of one or more rigid members 210. In such embodiments, the one or more inflatable members 230 can cause the one or more rigid members 210 to displace in a second end direction, away from the first end, responsive to the inflatable reservoir increasing in volume. In an embodiment, the one or more inflatable members 230 can cause the one or more rigid members 210 to displace in a first end direction, away from the second end, responsive to the inflatable reservoir decreasing in volume.

As shown in FIG. 2B, the one or more inflatable members 230 can be disposed adjacent to the longitudinal ends of the rigid members 210. In such embodiments, inflation of the inflatable members 230 can bias the rigid members 210 longitudinally toward each other. Deflation of the inflatable members 230 can cause the rigid members 210 move longitudinally away from each other. As shown in FIG. 2C, the one or more inflatable members 230 of the protective garment system 200' can be disposed adjacent to the lateral ends of the rigid members 210. In such embodiments, inflation of the inflatable members 230 can laterally bias the rigid members 210 towards each other. Deflation of the inflatable members 230 can cause the rigid members 210 to move laterally away from each other. When moved together in the second state, the rigid members 210 can provide protection or limit movement not present when the rigid members are separated by some distance in the first state. In an embodiment (FIG. 4A), a plurality of inflatable members 230 can be disposed on a single rigid member, such as multiple ends (or sides) thereof. In such embodiments, more than one of the inflatable members can be used to move the rigid member in more than one direction, such as longitudinally and laterally. In some embodiments, one inflatable member can move more than one rigid member. In an embodiment (FIGS. 3E and 3EE), the one or more inflatable members 230 can be associated with a rigid member 210 effective to cause the rigid member 210 to turn or pivot about a point (e.g., in relation to the supportive member or individual).

The controller 240 can be operably coupled to the one or more inflatable members. In such embodiments, the controller 240 can direct the one or more inflatable members 230 to alter or maintain the volume of the inflatable reservoirs therein, such as by directing the fluid source to alter or maintain the fluid supply thereto. In an embodiment, the one or more inflatable reservoirs can include one or more valves thereon configured to control the flow of fluid thereto or therefrom. In such embodiments, the controller 240 can be configured to control the one or more valves effective to control the volume of fluid therein.

In an embodiment, the one or more inflatable members 230 can cause the one or more rigid members to displace in a second end direction, away from the first end, in responsive to the inflatable reservoir decreasing in volume.

Figure 6:
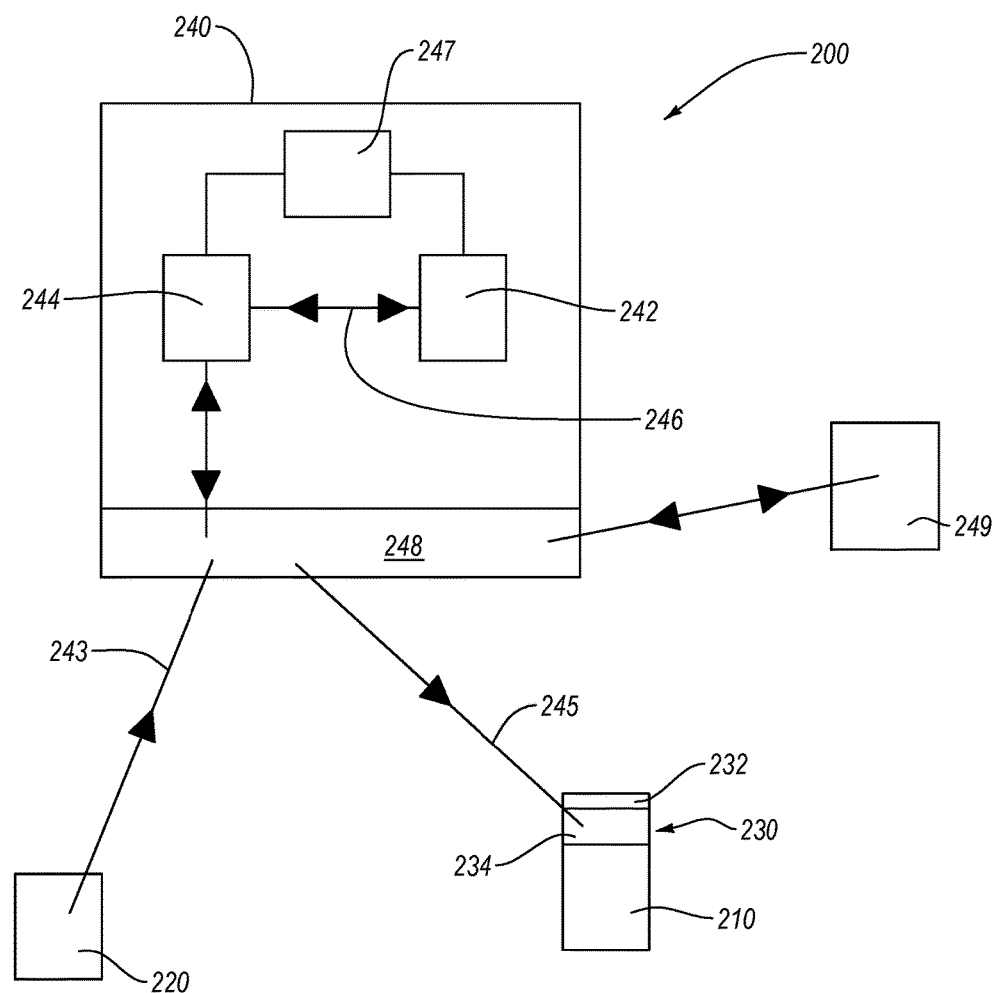
FIG. 6 is a block diagram of a protective garment system including a controller, according to an embodiment.

As discussed above, the protective garment system 200 includes the controller 240. The controller 240 can be operably coupled to one or more sensors 220, the plurality of inflatable members 230, or the at least one fluid source (described in detail below). The controller 240 can include a memory storage medium and a processor configured to access the memory storage medium (FIG. 6). In an embodiment, the controller 240 can include a user interface, such as one or more of a screen, a keypad, one or more buttons or switches, visual indicator(s) (e.g., LED lights), audio indicators (e.g., chimes), or haptic (e.g., vibration mechanism) indicators. The controller 240 can be operably coupled to and configured to receive sensed information from the one or more sensors (e.g., sensor data indicative of an actual impact or a potential impact). The controller 240 can be operably coupled to and configured to direct the one or more inflatable members 230 to change a volume of fluid therein. For example, the controller 240 can be operably coupled to the at least one fluid source and can be configured to direct the at least one fluid source to initiate, maintain, or cease a supply of fluid therefrom to the one or more inflatable reservoirs of the inflatable members 230. For example, the user interface or other output devices can indicate that the plurality of inflatable members 230 are deployed or are being deployed.

The controller 240 can be configured to direct the one or more inflatable members responsive to at least one of a sensed potential impact or actual impact. For example and as explained in more detail below with respect to FIG. 6, the controller 240 can be configured to determine from sensor data that at least one of an actual or potential impact to the garment system or individual wearing the same is occurring and, responsive thereto, direct the one or more inflatable members 230 (or the fluid source) to change a volume of fluid in the inflatable members (e.g., inflate) effective to move one or more rigid members 210. In an embodiment having sensors 220 in one or more regions, the controller can be configured to direct the at least one fluid source to controllably supply fluid to the one or more of the plurality of inflatable members 230 in only one or more selected regions of the protective garment system 200. Such systems can controllably offer protection substantially only at the sensed point of impact.

In an embodiment (FIGS. 2A and 2B), the controller 240 can be affixed to the supportive member 250. In an embodiment (FIG. 2C), the controller 240 can be remote from the supportive member 250, such as on a separate wearable device (e.g., a wristband), computer (e.g., desk-top or laptop), or mobile computing device (e.g., smartphone or tablet). In an embodiment, the protective garment system 200 can include more than one controller 240. For example, a protective garment system can include a plurality of controllers 240 each configured to receive sensor data from sensors in distinct regions of the garment system, or distinct sensor types (e.g., a controller receives accelerometer data and a second controller receives pressure data from the one or more sensors 220).

The supportive member 250 includes a substrate (e.g., fabric or material) that is at least one of conformed (e.g., contacting) or conformable to one or more body regions (e.g., physiological features) of the individual wearing the same. The supportive member 250 can support one or more of the plurality of rigid members 210, at least one of the one or more sensors 220, the one or more inflatable members 230, or the controller 240. As shown in FIGS. 2A-2C, the supportive member 250 can support the plurality of rigid members 210, one or more sensors 220, plurality of inflatable members 230, and in the case of protective garment system 200, the controller 240.

The supportive member 250 can be shaped and sized to receive one or more body parts of the individual therein. In some embodiments, the supportive member can include one or more garments, articles of clothing, or apparel, such as one or more of a jacket, a shirt, a vest, pants, shorts, socks, a hat, a jumpsuit, or a sleeve (e.g., a limb sleeve), etc. The plurality of rigid members 210 and the plurality of inflatable members 230 on the supportive member 250 can form part of one or more of apparel, sportswear, sports equipment, protective gear, or safety equipment. For example, the supportive member 250 can include protective gear such as a rib guard or hockey girdle. In some examples, the supportive member 250 includes supportive gear or apparel. In some embodiments, the supportive member 250 can include one or more of a helmet, a wrap (e.g., head, neck, leg, arm, abdominal, or other wrap), a brace (e.g., a leg brace, a back brace, or a neck brace), an athletic supporter, a panel, or one or more articles of clothing. In an embodiment, the supportive member 250 can include a bandage or a wound dressing.

In an embodiment, the supportive member 250 can include at least one layer of fabric. The at least one layer of fabric supports the components of the protective garment system. The fabric can include any of one or more a natural fabric (e.g., cotton, leather, wool, etc.), synthetic fabrics (e.g., nylon, polyester, neoprene, etc.), or one or more polymers (e.g., a plastic helmet). The at least one layer of fabric can include an outer surface (e.g., facing away from the individual wearer) and an inner surface (facing the individual). In such embodiments, any of the plurality of rigid members 210, the one or more sensors 220, the plurality of inflatable members 230, or the controller 240 can be disposed on any of the outer surface, the inner surface, or between the inner surface and the outer surface (e.g., embedded therein). In an embodiment, any of the plurality of rigid members 210, the one or more sensors 220, the plurality of inflatable members 230, or the controller 240 can be arranged in a layered configuration on one or more of the outer surface, the inner surface, or between the inner surface and the outer surface (e.g., embedded therein).

As shown in FIG. 2C, at least one of the components of the protective garment system 200' can be disposed on a separate article 260. For example, separate article 260 can include a wristband or computing device (not shown), such as a tablet computer, smartphone, or laptop.

The supportive member 250, the plurality of rigid members 210, and the inflatable members 230 can be sized, configured, and positioned to protect one or more regions of an individual 102 wearing the protective garment system 200. In an embodiment, each of the rigid members 210 and each of the inflatable members 230 of the protective garment systems 200, 200' can protect at least a torso of the individual, such as one or more of an abdomen, the thorax, an oblique, a lower back, or internal organs of an individual adjacent thereto. The rigid members 210 can be sized, positioned, shaped, and otherwise configured to at least partially conform to and protect one or more body regions (e.g., physiological features) of the individual wearing the same. The one or more body regions can include at least one of a head, an abdominal region (e.g., stomach, oblique) or organs internal thereto (e.g., spleen, liver, kidneys, or a vascular organ), an arm (e.g., elbow, upper arm, lower arm, or wrist), a leg (e.g., knee, calf, thigh, or ankle), a back, a chest, or a neck of the individual 102. The rigid members 210 conforming to body regions (e.g., physiological features) of the individual 102 can conform thereto singly or collectively. In an embodiment, each of the supportive member 250, the plurality of rigid members 210, and the plurality of inflatable members 230 are sized, positioned, and configured to provide skeletal support to one or more bones or joints in the body of an individual 102, such as upon inflation of the one or more inflatable members 230. For example, each of the supportive member 250, the plurality of rigid members 210, and the inflatable members 230 can be configured to prevent a joint from bending in an unhealthy manner (e.g., hyper-extending or twisting) upon changing to a second state responsive to a sensed potential or actual impact.

As described above, the protective garment systems disclosed herein can protect any number of body portions of an individual, which can vary from one embodiment to the next. FIGS. 2D-2G are respective schematics of supportive members according to one or more embodiments. Except as otherwise described herein, the supportive members and associated protective garment systems including their respective elements or components can be similar to or the same as any of the protective garment systems and their respective elements or components described herein.

In some embodiments, any of the protective members (e.g., rigid members), sensors, inflatable members, and/or controllers disclosed herein (collectively forming one or more protective garments) can be associated with (e.g., at least partially positioned in or on) any supportive member (e.g., garments) disclosed herein that can be worn by an individual. For example, FIGS. 2D to 2G are schematics of different supportive members that can include any of the protective members (and associated sensors, inflatable members, or controllers) disclosed herein, according to different embodiments. Except as otherwise described herein, the protective members (e.g., rigid members) shown in FIGS. 2D-2G and their materials, components, or elements can be similar or identical to the any of the protective members and their respective materials, components, or elements disclosed herein.

Referring to FIG. 2D, a supportive member 250d can be generally in the form of a shirt or other covering designed to cover at least a portion of a torso, abdomen, shoulders, or arm. The shirt can include a polo shirt, t-shirt, long-sleeved shirt, short sleeved shirt, sleeveless shirt, vest, jersey (e.g., football, baseball, basketball, soccer, hockey, or rugby jersey), sweatshirt, coat, jacket, protective gear (e.g., a rib vest), or any other garment or item (e.g., outerwear, innerwear) that at least partially covers an abdominal region, spinal region, back region, thoracic region, or at least a portion of an arm of an individual.

In an embodiment, the rigid members 210 (and one or more associated linkages, inflatable members, controller(s), or sensors (not shown)) can be positioned to at least partially protect at least one of the upper right portion (e.g., right hypochondrium), the upper central portion (e.g., epigastrium), upper left portion (e.g., left hypochondrium), the middle right portion (e.g., right lumber region), the middle central portion (e.g., umbilical region), the middle left portion (e.g., left lumber region), bottom right portion (e.g., right iliac fossa), bottom central portion (e.g., hypogastrium), or the bottom left portion (e.g., left iliac fossa) of the abdominal region. As such, the rigid members 210 can be positioned to protect at least one of a spleen, colon (e.g., right colon, sigmoid colon, descending colon), left kidney, right kidney, pancreas, liver, gallbladder, small intestine, large intestine, stomach, duodenum, adrenal glands, umbilicus, jejunum, ileum, appendix, cecum, urinary bladder, female reproductive glands, etc. In an embodiment, the rigid members 210 an be positioned to at least partially protect at least one of the right upper quadrant, the left upper quadrant, the right lower quadrant, or the left lower quadrant of the abdominal region. In an embodiment, the rigid members 210 can be positioned to at least partially protect a spine of the individual, such as at least one of the cervical spine (e.g., the shirt includes a collar), thoracic spine, lumbar spine, sacral spine, or tailbone. In an embodiment, the rigid members 210 can be positioned to at least partially protect a chest of an individual, such as at least one of the true ribs, false ribs, floating ribs, sternum, clavicle, the jugular notch, pectoral region, sternal region, etc. In an embodiment, the rigid members 210 can be positioned to at least partially protect a back of the individual, such at least one of lower back, upper back, scapular regions, interscapular region, lumbar region, sacral region, coxal region, inguinal region, gluteal region, etc. In an embodiment, the rigid members 210 can be positioned to at least partially provide skeletal support to at least one of the abdominal region, spinal region, back region, thoracic region, or arm of the individual.

In an embodiment, the rigid members 210 can be positioned to at least partially protect an arm of the individual, such as at least one of the shoulder, elbow, wrist, forearm, acromial region, brachial region, cubital region, antebrachial region, or another portion of the arm. In some embodiments, the supportive member 250 can comprise or be configured generally in a form of a glove, a sleeve, a shoulder brace, wrist brace, an elbow brace, or other gear or garment for covering a portion or all of an arm. In an embodiment, the rigid members 210 can be positioned to at least partially protect at least a portion of a hand of the individual, such as at least one of carpal region, palmar region, finger, or another portion of the hand. In embodiments, the supportive member(s) 250 can be generally in a form of a glove, a finger cot, or other gear or garment for covering a portion or all of a hand.

Referring to FIG. 2E, a supportive member 250e can include head-cover. The head-cover can include a baseball cap, football helmet, motocross helmet, safety helmet, scrum cap, bicycle helmet, hockey helmet, face mask, chin guard, mouth guard, glasses, or any other supportive member that at least partially covers a portion of an individual's head. For example, the rigid members 210 (and one or more associated linkages, inflatable members, controller(s), or sensors (not shown)) can be positioned to at least partially protect at least one of eyes, ears, nose, mouth, teeth, tongue, chin, jaw, cheek, facial region, cranial region, cervical region, nuchal region, forehead, temple, crown, nape of the neck, occipital protuberance, parietal ridge, side, top, or another portion of the head. In an embodiment, the rigid members 210 can be positioned to at least partially provide skeletal support to at least one of the head of the individual.

Referring to FIG. 2F, a supportive member 250f can include pants or similar garment or gear of any suitable length generally designed to cover at least a portion of each of two legs, or other garment or gear generally designed to cover at least a portion of at least one leg, or other garment or gear generally designed to cover at least a portion of a pelvis. For example, the supportive member can comprise full length trousers, shorts (e.g., basketball shorts), capri pants, skirts, dresses, kilts, jeans, leggings, football pants, baseball knickers, hockey pants, rugby trousers, knee brace, ankle brace, jockstrap, boxer briefs, or any other supportive member (e.g., outerwear, innerwear) that at least partially covers at least a portion of one or more of a leg, or a pelvic region of an individual. For example, the rigid members 210 (and one or more associated linkages, inflatable members, or sensors (not shown)) can at least partially protect at least one of toes, arch, heel, ankle, calf, shin, knee, thigh, male reproductive organs, female reproductive organs, lower abdominal region (e.g., iliac fossa), waist, rectal region, pubic region, coxal region, inguinal region, gluteal region, sacral region, lower lumbar region, perineal region, popliteal region, calcaneal region, crural region, tarsal region, dorsum of foot, patellar region, etc. The supportive member 250f can be configured as footwear (not shown), such as a sock, shoes, sandals, slippers, or any other item that covers at least a portion of a foot. For example, the protective garment 100v can at least partially protect at least one of a toe, arch, or heel. In an embodiment, the rigid members 210 can be positioned to at least partially provide skeletal support to at least one of the feet, legs, or pelvic region of the individual.

In some embodiments, the supportive member(s) can be configured generally in a form of a single unit of clothing (not shown) that substantially covers at least the majority of the torso or the majority of a body of the individual. For example, the supportive member(s) can be a jumpsuit, a flight suit, a unitard, a wetsuit, an undergarment (e.g., a union suit), etc. For example, the single unit of clothing can cover all of a limb (e.g., have long sleeves or long pant legs) or a portion of the limb (e.g., have short sleeves or short pant legs). In one example, an undergarment can be worn under additional protective gear, such as protective athletic gear, protective safety gear (e.g., fire protection) or protective environmental gear (e.g., SCUBA gear or a space suit).

In an embodiment, the supportive member can be sized, shaped, and otherwise configured to be worn by a nonhuman animal. For example, the supportive member can be configured to be worn by a rescue animal, such as a dog, or military animal, such as a dog or horse. For example, the supportive member might be configured to cover a torso, a pelvis, a shoulder, a leg, a paw or hoof, a head, a neck, or a spine of an animal. For example, the supportive member might be configured as a vest, a helmet, a neck cover, or a cover for a paw or leg.

Referring to FIG. 2G, a supportive member 250g can include a sleeve. The sleeve can be any item of clothing configured to protect only a single limb of an individual. As such, the rigid members 210 (and one or more associated linkages, inflatable members, or sensors (not shown)) can be positioned to at least partially protect at least one of a wrist, hand, elbow, shoulder, knee, ankle, calf, shin, or another suitable body part. In an embodiment, the rigid members 210 can be positioned to at least partially provide skeletal support to the individual.

Figure 3A:
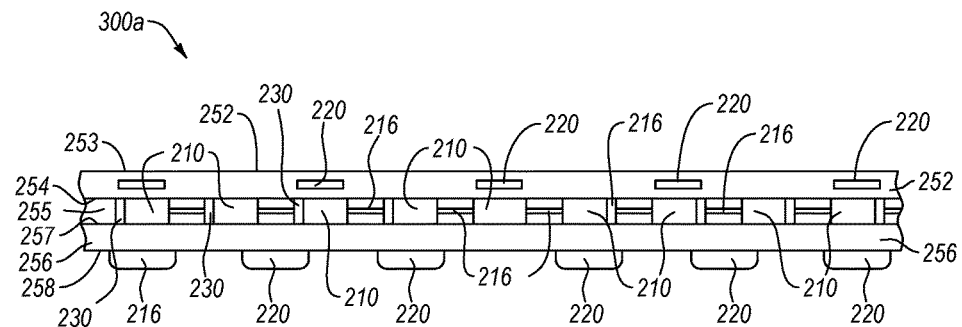
FIGS. 3A and 3B are cross-sectional views of a portion of the protective garment system of FIG. 2A taken along the plane A-A thereof, according to different embodiments.
Figure 3B:
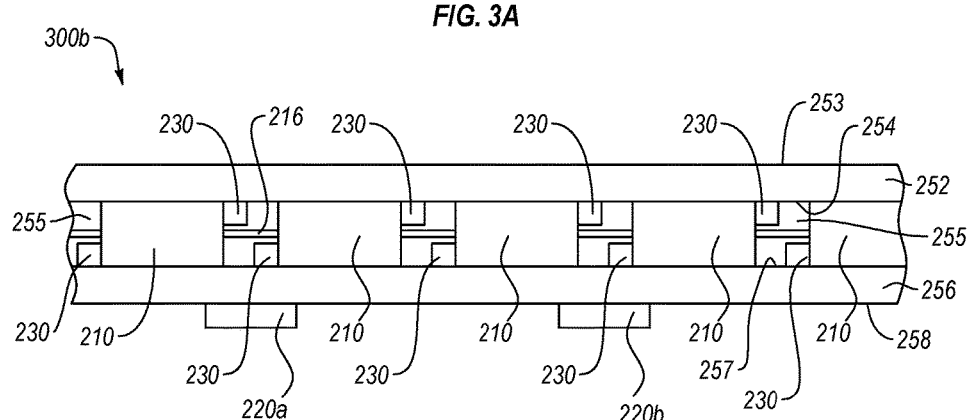

FIGS. 3A and 3B are cross-sectional views of a portion of the protective garment system of FIG. 2A taken along the plane A-A, according to different embodiments. In an embodiment, the supportive member 250 includes at least two fabric layers defining inner surface(s) and outer surface(s) of the supportive member 250. The two fabric layers can include an inner layer 252 proximate to the individual (not shown), and an outer layer 256 distal to the individual.

An inner surface 254 of the inner layer 252 and an inner surface 257 of the outer layer 256 can generally face each other and define an interior of region 255 of the supportive member 250. An outer surface 253 of the inner layer 252 and an outer surface 258 of the outer layer 256 can face away from each other and define the exterior regions of the supportive member 250. In such embodiments, at least one of the plurality of rigid members 210 or the plurality of inflatable members 230 can be at least partially disposed in the interior region 255.

As shown in FIG. 3A, the protective garment system 300a can include a plurality of sensors 220, at least one of which are embedded within the inner layer 252 of the supportive member 250 or at least one of which are on the outer region of the inner layer 252. In other embodiments, at least one of the one or more sensors 220 can be at least partially embedded within or on the outer layer 256. The interior region 255 can include one or more of the plurality of rigid members 210, the plurality of linkages 216, or the inflatable members 230 therein. In an embodiment, the interior region 255 can house one or both of the fluid source (not shown) or the controller 240 (not shown). As shown in FIG. 3A, each of the inflatable members 230 of the protective garment system 300a can be disposed on or adjacent to the rigid members 210 on an outermost surface thereof, such that the increase in volume of the inflatable members 230 laterally biases at least one of the rigid members 210 toward a central portion of the protective supportive member 250. In such embodiments, the central portion can be afforded additional protection of the rigid members 210 being biased thereto, and which may interlock or form a pattern as discussed below.

In an embodiment (not shown), the plurality of rigid members 210 can include a first layer of rigid members adjacent to the outer layer 256 (e.g., adjacent to the inner surface 257) and a second layer adjacent to the inner layer 252 (e.g., adjacent to the inner surface 254). In some embodiments, one or both of the layers of rigid members 210 can be inside or outside of the interior region). In an embodiment, the plurality of rigid members 210 can include a first layer of rigid members in the interior region 255 and at least second layer of rigid member in the outer region (proximate or distal to the individual wearer). Any of the first and second layers of rigid members can include one or more inflatable members therewith. In an embodiment, the first layer of rigid members and the second layer of rigid members can be coupled together by one or more or the plurality of inflatable members 230 disposed therebetween.

As shown in FIG. 3B, the supportive member 250 of protective garment system 300b can include the inner and outer layers 252 and 256, the interior region 255, and the external region. The interior region 255 can be defined as the space between the inner surface 254 of the inner layer 252 and the inner surface 257 of the outer layer 256. The interior region 255 can include the plurality of rigid members 210 and the plurality of inflation members 230 therein. The outer or exterior region can be defined as the space external to the outer surface 258 of the outer layer 256 and the outer surface 253 of the inner layer 252. The outer region of the supportive member 250 can include one or more sensors 220a or 220b thereon. The plurality of rigid members 210 can include an inflation member 230 at one or both of a first end and second end thereof. The second end can be generally opposite the first end. The inflation members 230 at the proximal and distal ends of the plurality of rigid members 210 can provide multi-directional or a directionally selective bias to the rigid members 210. For example, responsive to sensed potential impact or actual impact at the sensor 220b but not at sensor 220a, the controller 240 (not shown) can selectively direct the inflatable members 230 (and associated fluid sources) remote from the sensor 220b on a number of the rigid members 210 to inflate and bias the associated rigid members 210 inwardly towards the region of the sensor 220b. Similarly, the controller 240 can direct the inflatable members 230 nearest the sensor 220a to remain deflated, if no potential or actual impact is sensed. In some embodiments (not shown), one or more of the sensors 220a or 220b can be disposed internal to the outer surface(s) of the supportive member 250 such as within the interior region 255

In an embodiment, the rigid members can be arranged in multiple layers with one or more inflatable members therebetween. In such embodiments, an increase of the fluid (e.g., gas) in the inflatable reservoir of the one or more of the plurality of inflatable members causes at least one of the rigid members of the adjacent layers to move away from one another. In an embodiment, rigid members in adjacent layers can be at least partially bound together by the same inflatable member.

Figure 3C:
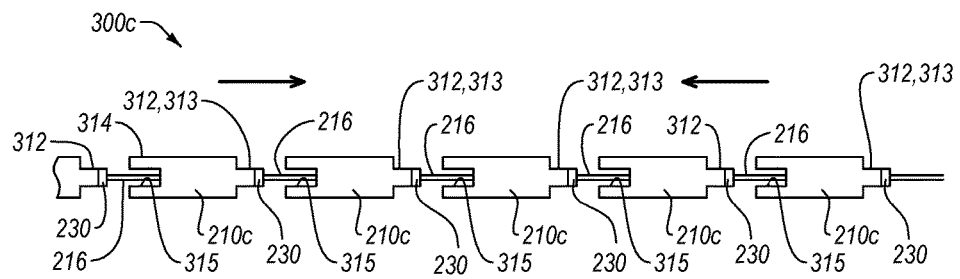
FIG. 3C is a schematic of a portion of a protective garment system, according to an embodiment.

In an embodiment, the plurality of rigid members can be configured to at least partially interlock with each other upon activation of the one or more inflatable members associate therewith. FIG. 3C is a schematic of a portion of a protective garment system 300c, according to an embodiment. The protective garment system 300c can include any of the components of the protective garment systems disclosed herein. The protective garment system 300c includes a plurality of rigid members 210c. Each of the plurality of rigid 210c members can be similar or identical to the rigid members 210 in one or more aspects. Each of the plurality of rigid members 210c is configured to interlock with at least one adjacent rigid member 210c. Each of the rigid members 210c can include a first end region 312 and a second end region 314. The second end region 314 can be generally opposite the first end region 312, such that a plurality of rigid members 210c can be linearly arranged first end region 312 to second end region 314 (of the adjacent rigid member) arrangement. The first end region 312 can be complementary configured to the second end region 314, such as one or more of fitting therein, locking therewith, reversibly engaging, or slidably engaging. The surfaces of the first end region 312 can define at least one protrusion 313, and the surfaces of the second end region 314 can define at least one pocket 315 configured to at least partially accommodate the at least one protrusion 313 therein. In an embodiment, the at least one protrusion 313 can be configured to one or more of slidably engage, reversibly engage, or at least temporarily lock into the at least one pocket 315. In an embodiment, one or more inflatable members 230 can be disposed adjacent to the first end region 312 or the second end region of one or more of the rigid members 210c, effective to provide a bias to move adjacent protrusions 313 into adjacent pockets 315. As shown, in an embodiment, only some of the plurality of rigid members 210c can have an inflatable member 230 associated therewith. Such inflatable members can be disposed on or adjacent to specific rigid members to cause one or more rigid members in a region to at least partially interlock with each other. For example, in FIG. 3C, the inflatable members 230 at generally opposite ends of the plurality of rigid members 210c can cause the plurality of rigid members 210c to at least partially interlock with each other. In such embodiments, the at least one pocket 315 and at least one protrusion 313 can be configured to provide structural support upon or responsive to locking together. Such structural support can resist impacts (e.g., from substantially orthogonal or oblique directions to the plurality of rigid members 210c), bending, twisting, concussive force, or other potentially injurious forces.

In an embodiment, first rigid member 210 can include only protrusions 313 thereon, the immediately adjacent rigid members can each include substantially only pockets 315 thereon, and so forth. In such embodiments, the rigid members can interlock with each of the adjacent rigid members having a complementary configuration.

In an embodiment, the plurality of rigid members can be configured to overlap one another upon inflation of one or more inflatable members. FIGS. 3D and 3DD are schematics of a plurality of rigid members 210 of the protective garment system 300d in a first state and a second state, according to an embodiment. The protective garment system 300d can include any of the components of the protective garment systems disclosed herein. The protective garment system 300d includes a plurality of rigid members 210d. Each of the plurality of rigid 210d members can be similar or identical to the rigid members 210 in one or more aspects. Each of the plurality of rigid members 210d is configured to overlap with at least one adjacent rigid member 210d. Each of the rigid members 210d can include an outer side 317 and an inner side 318. In an embodiment, the plurality of rigid members 210d can be arranged in a generally linear arrangement as shown, with each of the rigid members 210d being oriented at an oblique angle (e.g., less than 45 degrees) with respect to the generally linear arrangement of the plurality of rigid members 210d. In the first state shown in FIG. 3D, each of the plurality of rigid members 210d can be spaced from each other a distance, such as having a gap therebetween.

In the second state shown in FIG. 3DD, each the plurality of rigid members 210d can at least partially overlap at least one adjacent rigid member. For example, upon applying a bias inwardly along the length of the generally linear arrangement with inflatable members 230, a portion of the inner side 318 of a first rigid member 210d can generally overlap a portion of the outer side 317 of an adjacent second rigid member 210d. Also, the a portion of the outer side 317 of the first rigid member 210d can generally overlap a portion of the inner side 318 of an adjacent third rigid member 210d.

In an embodiment, rather than or in addition to having an angled orientation with respect to the overall arrangement of the plurality of rigid members, each of the rigid members may be offset from adjacent rigid members in a staggered arrangement. For example, two or more rows of rigid members can be offset from each other in a first direction and configured to at least overlap each other upon a bias from the first direction or a second direction substantially orthogonal to the first direction.

In an embodiment, the plurality to rigid members can be configured to form an array. For example, the array can include a first state where the plurality of rigid members are not in contact with each other and a second state wherein at least one of the rigid members to contact each other, such as interlocking or overlapping each other.

Figure 3E:
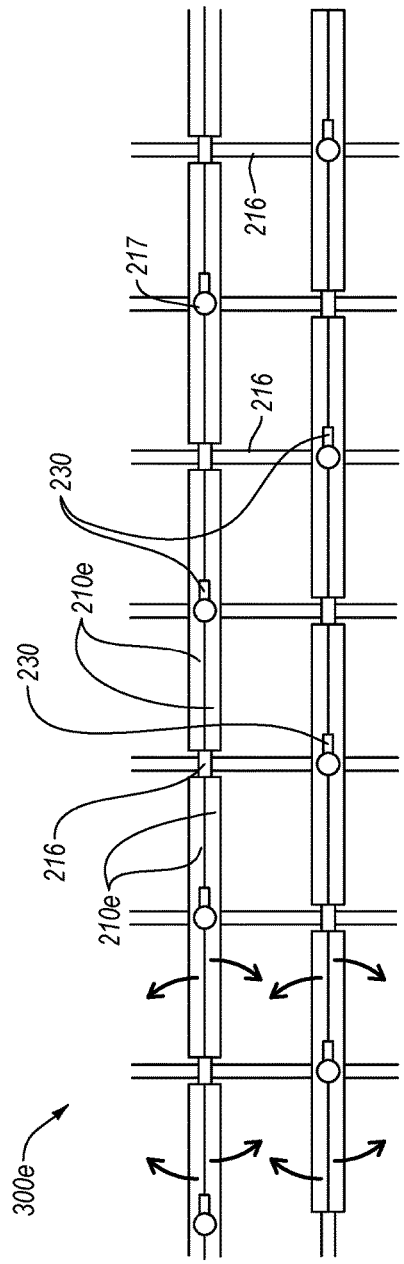
FIGS. 3E and 3EE are schematics of an array of rigid members of a protective garment system in a first and second state, respectively, according to an embodiment.
Figure 3E:
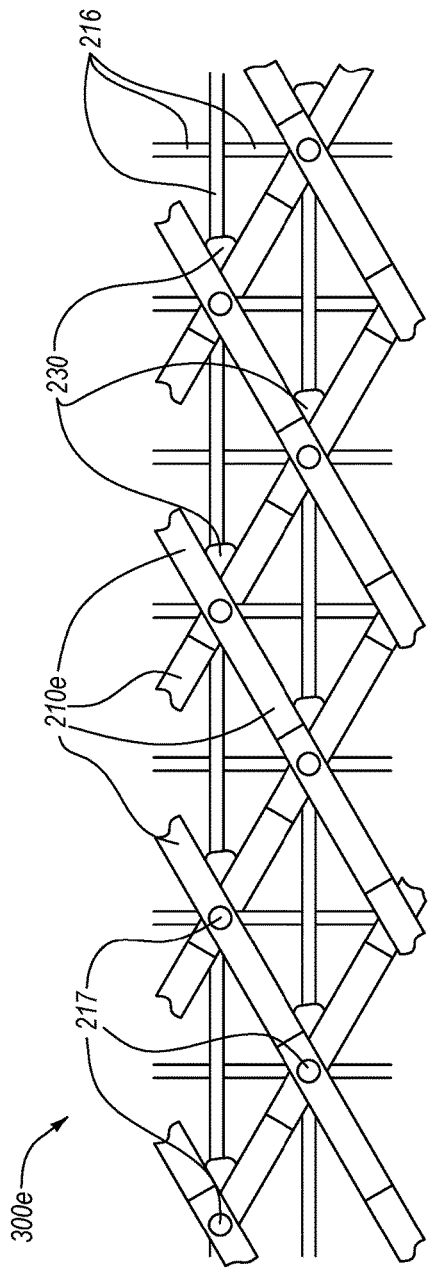

FIGS. 3E and 3EE are schematics of an array of rigid members 210e of a protective garment system 300e in a first and second state, respectively. As shown in FIG. 3E, in the first state, the plurality of rigid members 210e can be arranged in substantially parallel rows. The rigid members 210e in each row can be offset from the rigid members 210e in adjacent rows. In an embodiment, each of the rigid members 210e in the adjacent rows can be substantially parallel, both vertically and horizontally. Each of the rigid members 210e can be held in place by one or more linkages 216 therebetween. In an embodiment, each of the rigid members 210e can be configured to move about a pivot 217. The pivot 217 can support or otherwise be disposed between two rigid members 210e bound thereto. The pivot 217 can be a swivel, a button, an elongated member (e.g., a bar or shaft), etc. One or more rigid members 210e can be disposed at different points longitudinally along each pivot 217 (e.g., offset from each other along the pivot in a scissor or scissor-like arrangement). At least one of the rigid members 210e on a pivot 217 can have an inflatable member 230 associated therewith (e.g., adjacent or attached thereto). In an embodiment, one or more inflatable members 230 can be disposed between the rigid members 210e on the same pivot 217.

As shown in FIG. 3EE, the inflatable members 230 can be inflated and bias the rigid members 210e on each pivot 217 away from each other to induce the second state. The inflatable reservoirs of the inflatable members 230 can be sized and configured to move the rigid members 210e associated therewith a desired distance or angle about the pivot 217. In the second state, the rigid members 210e on adjacent rows of rigid members 218 can at least partially overlap, such as crossing the distal (from the pivot) ends of the rigid members 210e on adjacent rows. The overlapping rigid members on adjacent rows can provide an interlocking therebetween to provide structural protection. Such interlocking can provide more protection than the first state, such as impact resistance and structural support. In an embodiment, the rows of adjacent rigid members 210e can form an array. In an embodiment, only inflatable members 230 in specific portions of each row can be inflated responsive to a sensed potential or actual impact, to offer protection only to the specific region. In an embodiment, all of the inflatable members 230 in each row can be inflated responsive to a sensed potential or actual impact.

In an embodiment, each of the rigid members in plurality of rigid members (e.g., an array or row) can be one or more of the same shape, the same size, the same material, different shapes, different sizes, or different materials.

In some embodiments, each rigid member or each array of rigid members can include one or more inflatable members, one or more controllers, and/or one or more sensors associated therewith. For example, each rigid member in an array of rigid members can include a specific one of a plurality of inflatable members and sensors associated therewith to move the respective rigid member. In an embodiment, each rigid member includes at least one inflatable member, at least one controller, and at least one sensor. In some embodiments, an array of rigid members can include one sensor and at least one inflatable member, and at least one controller.

Figure 4A:
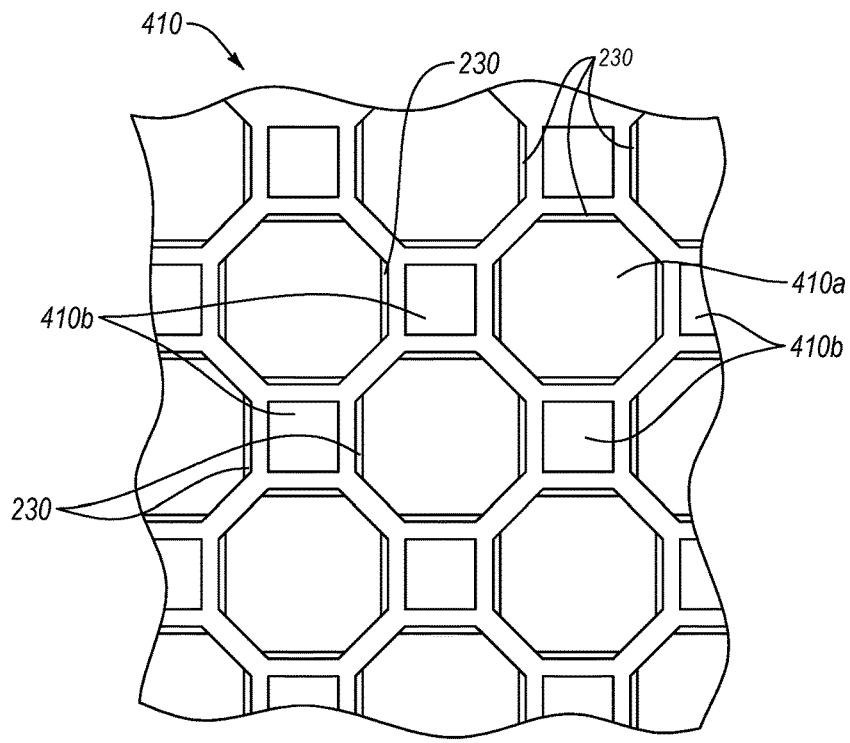
FIGS. 4A and 4B are front view schematics of an array of rigid members in a first state and a second state, respectively, according to an embodiment.
Figure 4B:
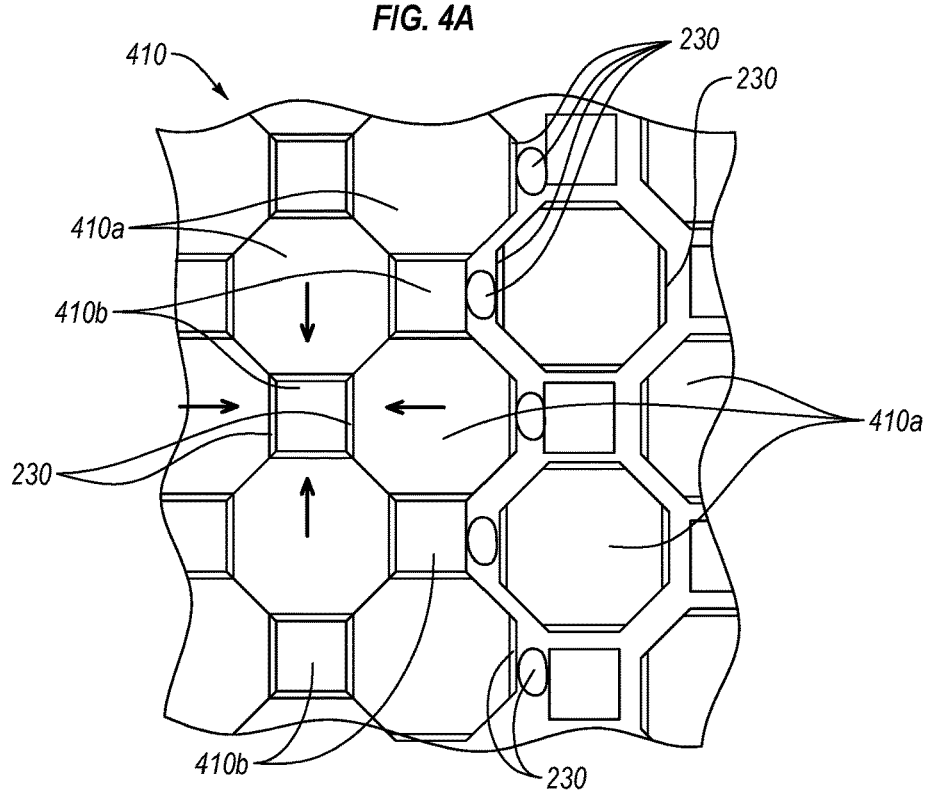

FIGS. 4A and 4B are front view schematics of an array of rigid members 410 in a protective garment system in a first state and a second state, according to an embodiment. In FIG. 4A, the array of rigid members 410 includes rigid members 410a and rigid members 410b. The rigid members 410a and rigid members 410b can be similar or identical to any of the rigid members disclosed herein in one or more aspects. Each of rigid members 410a is octagonal and each of rigid members 410b is substantially rectangular (e.g., square). While octagonal and rectangular rigid members 210a and 210b are depicted in FIGS. 4A and 4B, any of the shapes disclosed herein can be used. The individual rigid members 410b can fit between at least two (e.g., four or more) rigid members 210a adjacent thereto, effective to form an array of rigid members 410 having a repeating pattern of alternating (one or more of vertically or horizontally) rigid members 410a and 410b. In the first state each of the rigid members 410a and 410b can be spaced from an adjacent rigid member 410b or 410a.

In an embodiment, one or more of the rigid members 410a and 410b can include one or more inflatable members 230 associated therewith, such as contacting, adjacent thereto, or secured thereto. One or more of the rigid members 410a can include an inflatable member 230 associated with one or more end regions thereof, such as each of the vertical and horizontal ends of the rigid members 410a. In an embodiment, only certain ones of the plurality of inflatable members 230 can be selectively inflated to bias the rigid members 410a and 410b adjacent thereto in a selected direction. For example and as shown in FIG. 4B, in the second state, each of the inflatable members 230 around a specific region of a protective garment system can be selectively inflated (as directed by the controller responsive to sensing at least one of an actual or a potential impact) effective to cause the rigid members 410a and 410b to move inward toward the specific region and provide greater protection, such as by overlapping, interlocking, etc., therein. In such embodiments, an inflatable member 230 can move more than one rigid member 410a and/or 410b. For example, a single inflatable member 230 can move rigid members 410a and 410b in generally opposite directions upon inflation of the inflatable member 230 therebetween. A single inflatable member 230 can also move rigid members 410a and 410b in the same direction in a chain reaction type bias wherein the rigid member 410a can move according to pressure exerted thereon by the inflatable member 230, and in turn, apply a bias to and move the rigid member 410b adjacent thereto, in the same direction. Accordingly, single inflatable members 230 can move multiple rigid members 410a and 410b.

As shown in FIG. 4B, in an embodiment, only a portion of the array of rigid members 410 can be selectively moved into the second state. The remaining rigid members of the array can remain in the first state. The rigid members 410a and 410b in the specific region can be brought into contact with one another (on the left side of FIG. 4B), such as overlapping or interlocking; and the rigid members 410a and 410b outside of the specific region (on the right side of FIG. 4B) can remain spaced apart in the first state. In the first state, the plurality of rigid members, inflatable members, linkages, and supportive member can allow relatively greater freedom of movement and less structural support to an individual; while in the second state, the same can provide relatively reduced freedom of movement and greater structural support compared to the first state. Conversely, in an embodiment, in the first state, the rigid members, inflatable members, linkages, and supportive member can be configured to provide relatively less freedom of movement and greater structural support for an individual; while in the second state, the same can allow relatively greater freedom of movement and less structural support compared to the first state. In an embodiment, the rigid members, inflatable members, linkages, and supportive member can be configured to allow a plurality of intermediate states between the first state and the second state. For example, the inflatable members can be configured to be partially inflated and only partially move the rigid members, such as only moving the rigid members a portion of the distance that a full volume in the inflatable member would achieve. In an embodiment, the inflatable members can be controllably deflated to provide a second state, or an intermediate state after inflation (e.g., when an inflated stated is the first state). While discussed in terms of a first state or a second state in certain examples, the state in which the protective garment systems described herein provide protection from impact, bending, twisting etc., can be described as a deployment state. That is, a state in which the protective garment system is deployed to protect an individual. The non-deployment state can be described as the undeployed or inactive state.

While the array of rigid members 410 is shown in a substantially checker-board pattern, different patterns can include a sunburst pattern, a hexagonal pattern, a triangular pattern, a concentric pattern, a tessellating pattern, or any other suitable pattern. Arrays of rigid members can be sized and configured to cover specific regions of an individual. Such regions can vary in any of size, pattern, shape, type of rigid members therein (which can also vary in size and shape), and linkages.

Figure 5A:
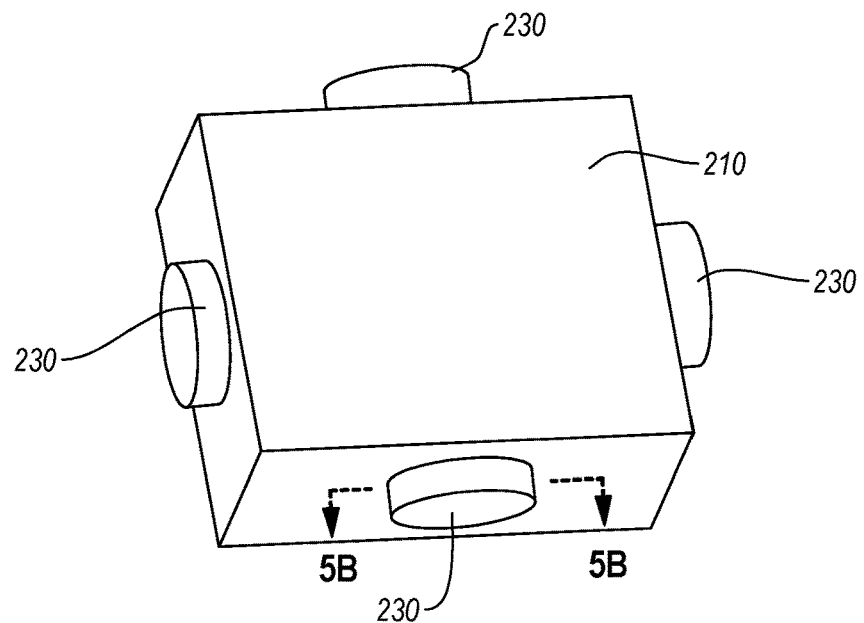
FIG. 5A is an isometric view of a rigid member having a plurality of inflatable members, according to an embodiment.
Figure 5B:
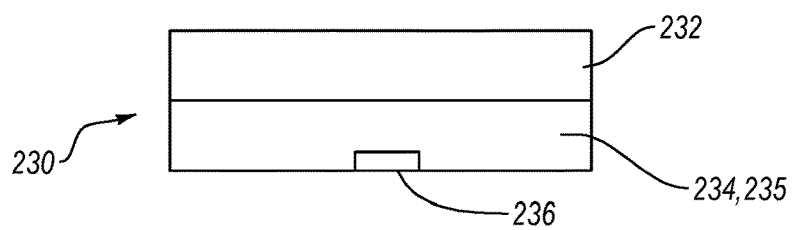
FIGS. 5B-5F are cross-sectional views of the inflatable member taken along the plane B-B in FIG. 5A, according to various embodiments.
Figure 5C:
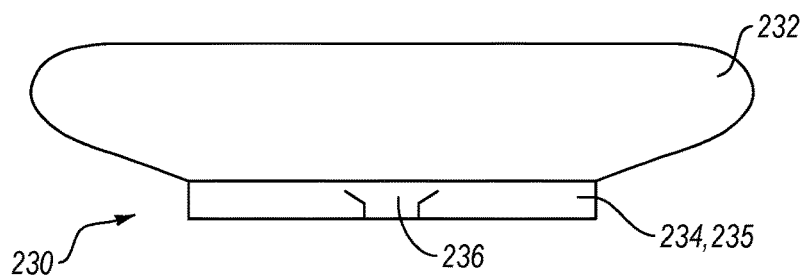

FIG. 5A is an isometric view of a rigid member 210 having a plurality of inflatable members 230. The inflatable members 230 can be configured and positioned in association with the rigid member(s) 210 effective to bias the rigid member(s) 210 a selected distance or a selected direction. One or more surfaces of the rigid member 210 can have one or more inflatable members 230 thereon. For example, the cuboid rigid member 210 can include an inflatable member 230 associated with (e.g., disposed in contact with, adjacent to, or secured to) each of four surfaces in single plane extending therethrough, such as a vertical (e.g., the x-z plane as shown) or horizontal plane extending through the cuboid rigid member 210. In such embodiments, the rigid member 210 can be selectively moved in any direction along the plane in which the inflatable members lie. For example, if the inflatable member 230 on the left side of the rigid member 210 is inflated, the rigid member 210 will be biased to the right. Additionally, a neighboring rigid member on the left side of the rigid member 210 can be biased to the left responsive thereto.

In an embodiment, all six surfaces of the rigid member 210 can have at least one inflatable member 230 associated therewith. In an embodiment, more than one inflatable member can be inflated at a time, such as to bias the rigid member in a diagonal direction. In an embodiment, an inflatable member 230 can be associated with an intersection of two or more surfaces thereof, such as at a corner of the cuboid rigid member 210. In some embodiment, and inflatable member 230 can be positioned on a rigid member 210 to move the rigid member 210 forward to a surface of the supportive member 250 or backward away from a surface of the supportive member 250. The shape of the rigid member 210 or inflatable member 230 can determined the distance that the rigid member 210 travels in response to the inflation of the inflatable member 230.

Figure 5D:
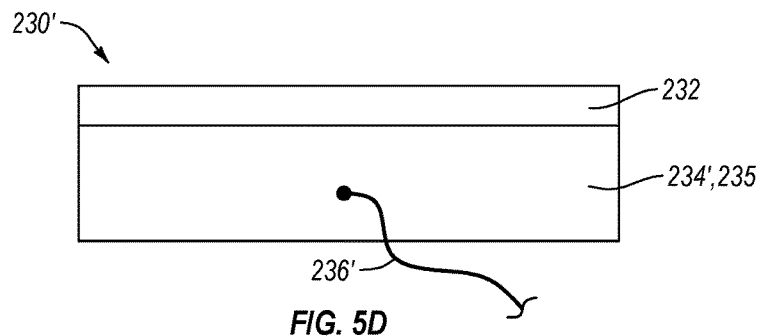
Figure 5E:
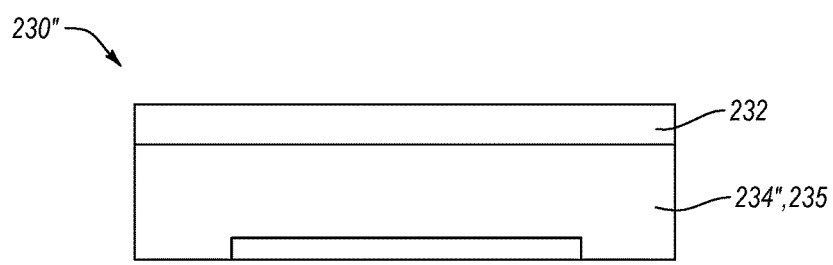
Figure 5F:
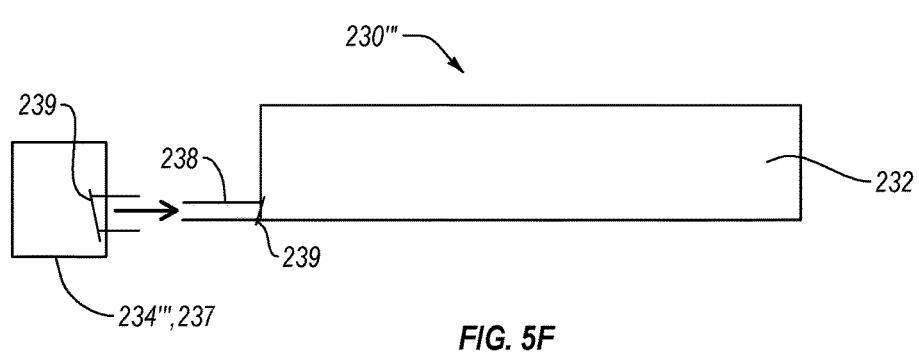

FIGS. 5B-5F are cross-sectional views of the inflatable member 230 taken along the plane B-B in FIG. 5A, according to various embodiments. FIGS. 5B and 5C are cross-sectional views of inflatable member 230 in an uninflated and inflated state, respectively. FIG. 5B depicts the inflatable member 230 in the uninflated state. The inflatable member 230 can include an inflatable reservoir 232 operably coupled to a fluid source 234. The fluid source 234 can be integral to the inflatable member 230 as shown in FIGS. 5B and 5C. In an embodiment, the fluid source can be remote from the inflatable reservoir 232 and fluidly coupled thereto by a conduit (FIG. 5F). The inflatable reservoir 232 can have a first volume in the uninflated state (FIG. 5B) and a second, larger volume in the inflated state (FIG. 5C).

The inflatable reservoir 232 can be constructed of any material suitable to hold a fluid therein. For example, the inflatable reservoir 232 can be constructed of rubber, silicon, a fabric (e.g., nylon fabric, polyester fabric, etc.), a polymer, a foil, or combinations of any of the foregoing (e.g., a rubber coated fabric). The inflatable reservoir 232 can be configured to increase in volume by about 50% or more, such as about 100% or more, about 150% or more, about 200% or more, about 300% or more, about 400% or more, about 500% or more, less than about 1000% increase in volume, or ranges thereof including any of the above values as endpoints. In an embodiment, the inflatable reservoir 232 can be configured to expand in volume between the inflated and uninflated states effective to move one or more rigid members a selected distance.

The fluid source 234 can be configured to supply one or more of a gas or a liquid to the inflatable reservoir(s) 232. As shown, in an embodiment, the fluid source 234 can be configured as a chemical cell 235 in fluid connection with the inflatable reservoir 232. The chemical cell 235 can include one or more reactants therein. The one or more reactants can be composed and configured to provide a fluid to at least partially fill the inflatable reservoir 232 upon reaction thereof. In an embodiment, the one or more reactants can include a first reactant and a trigger or an ignition source 236 (e.g., heat, second reactant, or a catalyst). In an embodiment, the ignition source 236 can be disposed adjacent to or within the first reactant, and be separated therefrom by one or more moveable barriers. The one or more moveable barriers can be electronically controlled to move by the controller 240 (not shown) or ruptured due to the reaction of the one or more reactants. In an embodiment, the one or more reactants can be stored in separate chemical reservoirs within the at least one fluid source. In an embodiment, the ignition source can include a mixer configured to mix the one or more reactants effective to cause or facilitate a reaction therebetween (e.g., a catalyst and reactant(s)). In some embodiments, the one or more moveable barriers can be configured to open, dissolve, burn away, melt, or otherwise cease to separate the first reactant from the ignition source (e.g., a second reactant or catalyst).

In an embodiment, the fluid source 234 can include one or more chemical reservoirs therein. Each chemical reservoir can be configured to provide or react one or more metered doses of the one or more reactants responsive to direction from the controller. In an embodiment, multiple chemical reservoirs in a fluid source can each provide a single dose of chemical reactants effective to fill one or more inflatable reservoirs 232. In such embodiments, a single fluid source can incrementally or repeatedly fill one or more inflatable reservoirs 232.

As shown in FIG. 5C, responsive to moving, the ignition source 236 can contact the one or more reactants and cause a reaction therebetween effective to produce enough fluid (e.g., gas) to at least partially fill the inflatable reservoir 232. The one or more reactants can include any reactants suitable to produce a fluid in a short amount of time (e.g., millisecond scale evolution of fluid), such as those reactants used in the airbag industry. The one or more reactants can include one or more fuels and one or more oxidizers. For example, the one or more reactants can include an azide (e.g., sodium azide or strontium azide), potassium oxide, silicon dioxide, potassium nitrate, sodium oxide, ammonium nitrate, etc.

FIG. 5D is a cross-sectional view of an inflatable member 230' in which the ignition source 236' is configured as an electrode. The electrode can include one or more wire leads, bare wire(s), a spark plug (e.g., a mini- or micro-sized spark plug or coil), or any other spark source. The ignition source 236' can be controlled by the controller 240 (not shown) to selectively provide electrical stimulation effective to cause the one or more reactants in the fluid source 234' configured as a chemical cell 235 to react and produce a large amount of fluid (e.g., enough to at least partially fill the inflatable reservoir 232) in a short amount of time (milliseconds). The ignition source 236' can be configured to supply a desired amount of voltage and amperage for a selected duration effective to cause the reaction between the reactants in the chemical cell 235.

FIG. 5E is a cross-sectional view of an inflatable member 230" in which the ignition source 236" is configured as a heat source. The heat source can include a wire lead, a heating element, a glow plug, or one or more chemical reactants (e.g., hot burning compounds, such as alkali or alkaline earth metal containing compounds), or combinations of any of the foregoing. The ignition source 236" can be controlled by the controller 240 (not shown) to selectively provide thermal stimulation effective to cause the one or more reactants in the fluid source 234" configured as a chemical cell 235, to react and produce a large amount of fluid, such as a gas, in a short amount of time. The ignition source 236" can be configured to supply a desired amount of thermal energy for a desired duration effective to cause the reaction between the reactants in the chemical cell 235. The ignition source 236" can be configured as a heating element operably coupled to a power supply effective to provide electricity to provide resistive heating to the heating element. In such embodiments, the material in the heating element can be selected to provide a sufficient amount of heat in a short enough amount of time to allow the chemical reactants to react, produce a fluid, inflate the inflatable reservoir, and move the rigid members prior to provide protection to an individual.

FIG. 5F is a cross-sectional view of an inflatable member 230''' in which the fluid source 234''' includes at least one separate fluid reservoir 237, remote from the one or more inflatable reservoirs 232. The at least one separate fluid reservoir 237 can be configured as a compressed gas reservoir, a liquid reservoir, or any other reservoir. The compressed gas can include one or more of nitrogen, helium, oxygen, or any other compressible gas. The separate fluid reservoir 237 can include a pressure generating device (not shown) configured to provide enough pressure to force the fluid from the separate fluid reservoir 237, such as a mechanically- or electromechanically actuated bellows or piston. In an embodiment, each of the inflatable reservoirs 232 can be operably coupled to the same separate fluid reservoir. In an embodiment, a plurality of separate fluid reservoirs can be used. In such embodiments, the each of the separate fluid reservoirs 237 can be operably coupled to a plurality of inflatable members only in a specific region of the protective garment system, such that each separate reservoir 237 inflates only the members in one region of the protective garment system.

The separate fluid reservoir(s) 237 can be operably coupled to the one or more inflatable reservoirs via one or more conduits 238. The one or more conduits 238 can be constructed of fluid tight material, such as a polymer (e.g., PVC, an acetate, etc.) or metal tubing. In an embodiment, the conduits 238 can be flexible.

In an embodiment, one or more valves 239 can be disposed on one or more of the conduits 238, the inflatable reservoir 232, or the separate fluid reservoir 237. Each of the valves 239 can be operably coupled to and controlled by the controller 242 (not shown) to increase, maintain, or decrease the volume of fluid in the inflatable reservoir(s) 232.

In an embodiment, the separate fluid reservoirs 237 and one or more chemical reservoirs 235 can be operably coupled to the same inflatable reservoir 232 or separate inflatable reservoirs in the same protective garment system. In such embodiments, the chemical reservoirs 235 can be used to produce a fluid in the separate fluid reservoir 237, which can be directed to the inflatable reservoir(s) 232 via the conduit 238.

In an embodiment, at least one of the plurality of rigid members 220 can additionally or alternatively include one or more inflatable members 230 associated therewith (positioned and configured) to provide impact resistance upon inflation of the inflatable reservoir(s) associated therewith. For example, at least one inflatable member 230 can be used to at least partially absorb impact forces upon, or brace anatomical structures of, the individual, without regard to the associated rigid members.

FIG. 6 is a block diagram of the protective garment system 200 including at least one controller 240, according to an embodiment. The at least one controller 240 can include at least one memory storage medium 242 and at least one processor 244 including processing electrical circuitry operably coupled to the at least one memory storage medium 242. The at least one controller 240 can include an interface 248. The at least one controller 240 can be configured to determine if a deployment condition is required for at least one of the plurality of inflatable members 230 based at least partially on the one or more sensors 220 sensing at least one of a potential impact or an actual impact of the individual. The at least one controller 240 can be operably coupled to at least one of the plurality of inflatable members 230 and fluid sources 234 associated therewith; and at least one of the one or more sensors 220. The at least one controller 240 can control some or all of the inflatable members 230 and associated fluid source(s) 232 to supply or change a volume of fluid in the inflatable members 230 effective to move (relative to each other) one or more rigid members 210 associated therewith. The controller 240 can direct the inflatable members 230 and associated fluid source(s) 232 responsive to at least one of the sensed potential or actual impact. In an embodiment, the controller 240 can be configured to inflate only those inflatable members 230 in a region at and adjacent to a sensed actual or potential impact.

In an embodiment, the at least one controller 240 can include multiple controllers 240, each operably coupled to at least one of the one or more sensors 220. For example, a protective garment system can include a plurality of controllers 240, each operably coupled to one or more sensors 220 and one or more inflatable members 230 (and associated fluid sources) in a distinct region, and each configured to determine if a distinct region (or distinct rigid member 210) is experiencing at least one of an actual or potential impact. Responsive to the determination, each controller 240 can direct the one or more inflatable members 230 in the distinct region to increase an internal volume of the inflatable reservoir thereon, effective to move one or more rigid members 210 associated therewith. In an embodiment, each of the plurality of controllers can be configured to communicate with others controllers of the plurality of controllers.

The at least one memory storage medium 242 can include any non-transitory memory storage medium, such as a hard-disk drive, a solid state memory device, a flash drive, or the like. The at least one memory storage medium 242 can include one or more of program instructions for the processor 244, data from the one or more sensors 220 (e.g., present or previous sensed motion characteristics such as potential impacts, actual impacts, or forces associated therewith), threshold values for one or more forces or characteristics sensed by the one or more sensors 220, a history of the protective garment system (e.g., deployment or inflation history of each inflatable member, current status of the protective garment system, etc.), look-up tables corresponding to any of the proceeding, or system diagnostic statuses (e.g., current and past statuses, or readiness states of any components of the system).

The at least one processor 244 can be operably coupled to the at least one memory storage medium 242 via the connection 246. The at least one connection 246 can be a wireless connection or a hardwired connection. The at least one processor 244 is configured to access and read the memory storage medium 242. The at least one processor 244 is configured to receive sensor data indicating a potential or actual impact. The at least one processor is configured to direct the one or more inflatable members or fluid sources associated therewith to control (e.g., increase, decrease, or maintain) the volume of fluid in the inflatable reservoir 232 thereof.

The at least one processor 244 can determine if a deployment (e.g., protection) condition is required based on information from the one or more sensors 220. For example, the one or more sensors 220 can sense one or more objects within a specific proximity of the protective garment system (or individual wearing the same) and the processor 244 can determine if the proximity is below a threshold value for safety such as an impart or injury threshold value. In an embodiment, the one or more sensors 220 can sense a velocity of the one or more objects (e.g., the ground or a car) relative to the individual (or vice versa) or one or more sensors 220, and determine if the velocity is indicative of a potential impact therewith. In an embodiment, the one or more sensors 220 can be configured to sense a force or pressure applied thereto, and the processor 244 can determine if an actual or potential impact is taking place based on sensor data (e.g., of the sensed force or pressure). For example, one or more sensors 220 can be configured to sense a pressure applied thereto, and the processor can determine if the pressure is indicative of a force capable of injuring an individual, such as by comparing the measured force to a threshold force stored in the memory. The threshold levels can be set for any condition, such as the amount of pressure applied or potentially applied thereto, the size of object impacting or potentially impacting the garment system, the velocity of object impacting or potentially impacting the garment system, the orientation of one or more portions of the garments system such as twisting, falling, or bending, or combinations thereof. For example, the threshold value can be set by the individual, a medical professional, a manufacturer, the controller, or other persons.

Condition values beyond threshold levels or values can indicate the need for deployment conditions. The processor 244 can compare the sensed conditions, such as velocity, pressure, proximity, etc., to one or more threshold values to determine that an actual or potential impact is taking place. Responsive to a sensed characteristic (e.g., force, pressure, velocity, proximity, etc.) being beyond the corresponding threshold value, the processor 244 can direct the one or more inflatable members 230 and associated fluid sources (e.g., all inflatable members 230 or only those in the region adjacent to the sensors 220) to increase or decrease the fluid volume therein, effective to cause one or more rigid members 210 associated therewith to move from a first state to a second state (e.g., deployed state). In an embodiment, the at least one processor 244 can be configured to determine if a potential impact or actual impact is taking place based on a combination of any of the sensed characteristics disclosed herein.

Responsive to the determination of a required deployment condition (e.g., a change in states), the processor 244 can direct the one or more fluid sources to supply fluid to one or more of the inflatable members 230, effective to change the volume of fluid therein and move one or more rigid members 210 associated therewith.

The processor 244 can be configured to determine if a threshold level has been met or exceeded by a differential of one or more sensed characteristics sensed at adjacent sensors of the one or more sensors 220. For example, a single sensor 220 in a plurality of sensors 220 detecting a specific amount of pressure in a specific region of a supportive member can indicate a puncture wound is likely as compared to the same pressure spread out over a larger surface area. Responsive thereto, the processor 244 can direct the one or more inflatable members 230 to inflate and move the associated rigid members 210 to prevent puncture or blunt force injury. In an embodiment, a threshold level can include a level of pressure applied over a surface area whereby the threshold level corresponds to a force indicative of a possible puncture that would result from a relatively sharp object. In an embodiment, from sensor data from the plurality of sensors 220, the processor 244 can determine a level of acceleration or deceleration indicative of a force capable of breaking bone of the individual, or a motion and directions thereof (e.g., twisting or bending) indicative of a force capable of damaging a body part of the individual. Suitable threshold levels can be stored in the memory storage medium 242.

The processor 244 can be configured to set or adjust one or more threshold levels based on one or more of a velocity of at least one body part of the individual (e.g., how fast is a football player running), one or more physiological attributes of the individual (e.g., weight, height, age, health, etc.), a location of the individual with respect to one or more objects, a location of the individual within an area (e.g., if the individual is within a playing field), a time of day, an elapsed time (e.g., the time the individual has been playing or if the individual has been playing for a pre-determined amount of time), a history of impacts to at least a portion of the supportive member or protective member (e.g., a portion housing the sensor sensing current conditions), a history of deployment of the protective member (e.g., to the same portion housing the sensor sensing current conditions), or an activity level of the individual. That is, the processor 244 can be configured to adjust the threshold levels to compensate for velocity of a person, size of a person wearing the protective garment system, proximity of the individual to adjacent objects, or any other criteria.

In an embodiment, the processor 244 can be configured to search the deployment history of the inflatable members therein and at least partially base deployment determinations thereon. For example, the processor 244 can note a region where multiple impacts have taken place (as determined from multiple deployments) and inflate the inflatable members therein to provide added protection from repetitive injury to the individual in that region.

In an embodiment, the processor 244 can be configured to control the latches between one or more rigid members. The processor 244 can be configured to cause the latches to disconnect before, or during inflation of deflation of the one or more inflatable members. The processor 244 can be configured to cause the latches to reconnect after inflation or deflation of the one or more inflatable members. Such direction can be responsive to a determination by the processor that a deployment condition is or is not required, a signal or programming, or after a duration of time has passed.

As discussed above, the controller 240 can include the interface 248. The interface 248 can be configured to communicate with one or more of a user, a computing device, a tablet, a mobile computing device (e.g., a smartphone), or a remote control. The interface 248 can include a screen, an input device, a transceiver, or relay. For example, the interface 248 can relay sensed information signals 243 from the sensors 220 to the processor 244 or memory storage medium 242, and can relay control signals 245 to the one or more inflatable members 230 or fluid sources 234. In an embodiment, the sensed information signals 243 and control signals 245 can be relayed directly between the processor 244 and sensors 240, the one or more inflatable members 230, or fluid sources 234. Such sensed information or signals 243 and 245 can be transmitted and received via a wireless connection (e.g., Wi-Fi, infrared, Bluetooth, etc.) or a hard-wired connection.

In an embodiment, the interface 248 can include a user interface 249 configured to inform a user (e.g., the individual) of information relating to the system. The user interface 249 can include one or more output devices such as a screen, chime, one or more LED lights, or haptic indicator and one or more input devices (such as a keyboard, buttons, levers, switches, or dials). The user interface 249 can include a desktop computer, a laptop computer, a tablet computer, a mobile computing device (e.g., smart phone), a watch, or a remote control. The user interface 249 can be configured to output information to the user and accept input from the user. For example, the user interface 249 can be configured to output or communicate to a user (e.g., individual wearer, medical professional, coach etc.) one or more of previous impacts against the individual, a deployment history of the plurality of inflatable members, sensed motion characteristics, a readiness status of one or more portions of the protective garment system, program instructions, or threshold levels of force applied or predicted to be applied to the individual. The interface 248 and user interface 249 can be configured to receive one or more of input, instructions, or programming from one or more of the individual, the user, a mobile computing device (e.g., smartphone), a tablet, or a computing device.

The controller 240 can include a power source 247 operably coupled thereto. The power source 247 can be operably coupled to (e.g., hard-wired or wirelessly) one or more of the processor 244, the memory storage medium 242, the interface (including or excluding the user interface), the one or more sensors 220, the plurality of inflatable members 230, or the fluid source 234. The power source 247 can include one or more of a battery, a solar cell, a kinetic energy harvester, or a wall plug. In some embodiments, the power source 247 can be disposed on or in the controller 240. In some embodiments, the power source 247 can be located remotely from the controller 240, such as connected by one or more wires, or a wireless connection (e.g., induction charging).

Figure 7A:
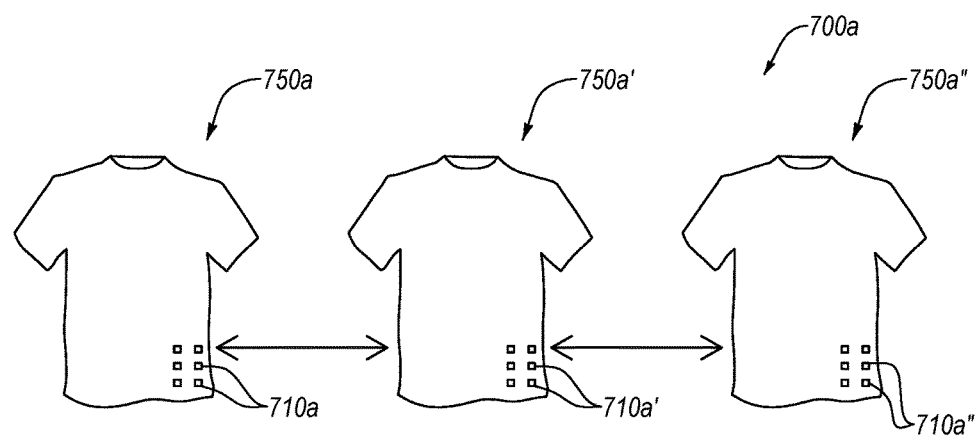
FIG. 7A is a schematic of a protective garment system that includes a plurality of garments, according to an embodiment.

Any of the supportive members (e.g., garments) and associated protective members (e.g., rigid members), sensors, inflatable members, and/or controllers disclosed herein (collectively forming one or more protective garments) can be used in a system having multiple supportive members and protective members. FIG. 7A is a schematic illustration of system 700a that includes a plurality of supportive members 750a, 750a', 750a" (each having one or more rigid members 710a, 710a', 710a", inflatable members, sensors, linkages, or controller(s) (not shown) as disclosed hereinabove), according to an embodiment. Each of the supportive members 750a, 750a', 750a" includes at least some rigid members 710a, 710a', 710a". The supportive members 750a, 750a', 750a" and the rigid members 710a, 710a', 710a" illustrated in FIG. 7A (and associated inflatable members, sensors, linkages, controller(s) (not shown) and their materials, components, or elements can be similar or identical to any of the rigid members (and associated inflatable members, sensors, linkages, controller(s)) disclosed herein.

In some embodiments, the supportive members can be worn by multiple individuals (e.g., the protective garments can be configured as shirts that can be worn by multiple individuals). Additionally or alternatively, the multiple supportive members can be worn by the same individual (e.g., multiple garments that can protect corresponding body portions of the individual). For example, multiple supportive members can be worn on a single individual or by multiple individuals such as wearing supportive members configured as a shirt and pants.

In an embodiment, the supportive members 750a, 750a', 750a" are communicably coupled together. For example, at least one of the supportive members 750a, 750a', 750a" includes a controller (not shown). The controller can be at least partially positioned on or distinct from at least one of the rigid members 710a, 710a', 710a". The controller can include a transceiver configured to communicate with at least one other supportive member 750a, 750a', 750a". In another example, at least one of the supportive members 750a, 750a', 750a" includes a communication device (e.g., at least one of a receiver, a transmitter, or a transceiver) distinct from the controller. The communication device can be communicably coupled to the controller of a supportive member 750a, 750a', 750a" and at least one other supportive member 750a, 750a', 750a".

The supportive members 750a, 750a', 750a" that are communicably coupled together can transmit one or more system signals to each other. The system signals can include location, speed, a direction of movement, or acceleration of at least one of the supportive members 750a, 750a', 750a" and the operation of the supportive members 750a, 750a', 750a" can be controlled responsive to receiving the system signals. The system signals can include one or more sensing signals, one or more operational instructions, one or more command signals (e.g., a controller of one of the supportive members 750a, 750a', 750a" can at least partially control the operation of another supportive member 750a, 750a', 750a"), one or more programs, information from a database, etc.

In an embodiment, each of the supportive members 750a, 750a', 750a" can be substantially similar or the same. In an embodiment, at least one of the supportive members 750a, 750a', 750a" can be different than another supportive member 750a. For example, at least two of the supportive members 750a, 750a', 750a" can include at least one of different components (e.g., different rigid members, different linkages, different inflatable members, etc.) a different arrangement of layers, the rigid members 710a, 710a', 710a" can be positioned to at least partially protect different parts of the body, different types of supportive members (e.g., shirts, hats, pants, or sleeves), etc.

Figure 7B:
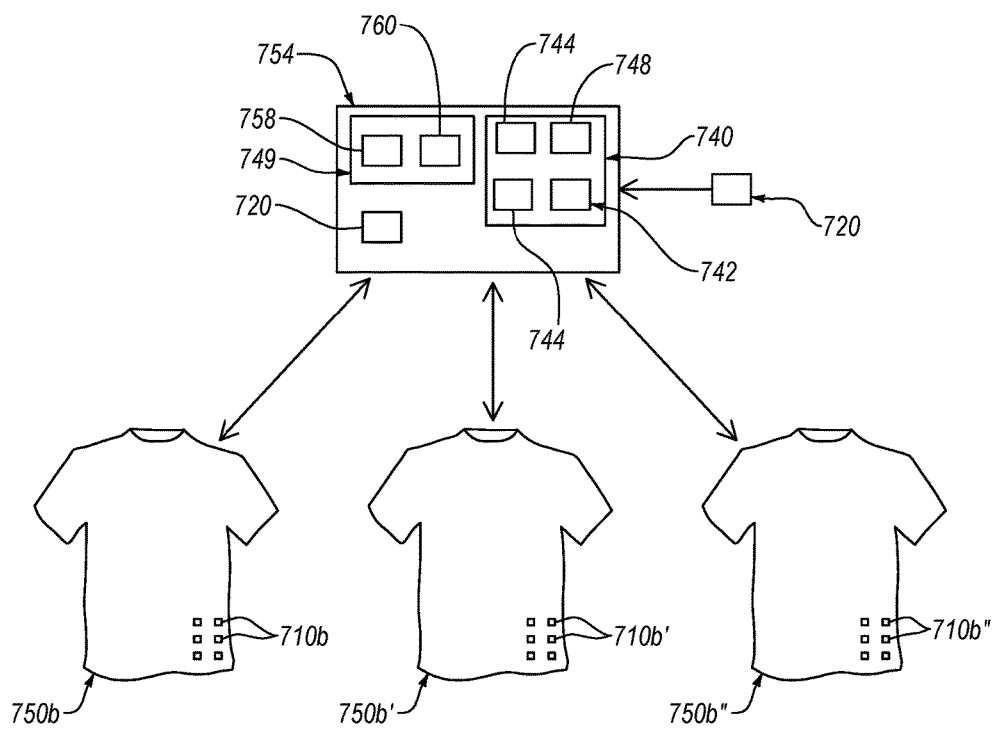
FIG. 7B is a schematic of a protective garment system that includes a plurality of garments, according to an embodiment.

FIG. 7B is a schematic of a system 700b that includes a plurality of supportive members 750b, 750b', 750b", according to an embodiment. Except as otherwise described herein, the supportive members 750b, 750b', 750b" can be similar or identical to the supportive members 750a, 750a', 750a" (FIG. 7A) and their respective materials, components, or elements. For example, each of the supportive members 750b, 750b', 750b" can include rigid members 710b, 710b', 710b" (and associated inflatable members, sensors, linkages, controller(s)) such as any of those disclosed herein.

As noted, the system 700b includes a plurality of supportive members 750b, 750b', 750b" that each include rigid members 710b, 710b', 710b" configured to protect one or more portions of an individual. At least some of the supportive members 750b, 750b', 750b" can be communicably coupled together. The system 700b also includes a central computing unit (CCU) 754. The CCU 754 can be communicably coupled to at least one of the supportive members 750b, 750b', 750b". The CCU 754 can include at least one of a laptop, desktop computer, tablet, cellular device, remote control, or another suitable electronic device. The system 700b can further include one or more sensors 720 configured to sense one or more characteristics of the system 700b. The sensors 720 can include any of the sensors disclosed herein. The one or more sensors 720 can be at least partially positioned in or on at least one of the supportive members 750b, 750b', 750b"; the CCU 754; or another structure at least proximate to the supportive members 750b, 750b', 750b" (e.g., sensors 720 setup around a playing field, in a stadium, etc.).

The CCU 754 can include a CCU controller 740 that is communicably coupled to one or more components of the system 700b. For example, the CCU controller 740 can be communicably coupled to at least one of the supportive members 750b, 750b', 750b" (e.g., at least one controller of at least one of the rigid members 710b, 710b', 710b"), the sensors 720, another component of the CCU 754, or another component of the system 700*b*. In an embodiment, the CCU controller 740 includes at least one processor 744 that is configured to at least partially control the operation of at least one of the components that are communicably coupled to the CCU controller 740.

In an embodiment, the CCU controller 740 can include memory storage medium 742. The memory storage medium 742 can include any of the memory storage mediums disclosed herein. The memory storage medium 742 can store at least one of one or more operational instructions, programs, or databases thereon. The databases can include information regarding at least one of actual impact or potential impact against at least one of the supportive members 750*b*, 750*b'*, 750*b"*, information about at least one of the supportive members 750*b*, 750*b'*, 750*b"*, medical history of at least one individual wearing at least one of the supportive members 750*b*, 750*b'*, 750*b"*, the sensing signals or another signal received at the CCU controller 740, or any other suitable database. The one or more operational instructions can include how to determine the one or more recommendations, when to provide or deny access to at least one of the databases, programs that are to be executed by the at least one processor 744, etc. The at least one processor 744 is communicably coupled to the memory 720. The at least one processor 744 can be similar or identical to any processor disclosed herein.

In an embodiment, the CCU 754 includes an interface such as a transceiver 748. The transceiver 748 can form a part of the CCU controller 740 or can be distinct from and communicably coupled to the CCU controller 740. The transceiver 748 is configured to communicably couple the CCU 754 to at least one supportive member 750*b*, 750*b'*, 750*b"*, the sensors 720, or another components of the system 700*b*. For example, the transceiver 748 is configured to receive or transmit at least one of one or more sensing signals, one or more information signals, one or more operational instructions, one or more command signals, or one or more system signals.

In an embodiment, the CCU 754 also includes a user interface 749. The user interface 749 enables the CCU 754 to communicate with an entity. The entity can include an individual wearing at least one of the supportive members 750*b*, 750*b'*, 750*b"*, a user of the CCU 754 (e.g., medical personnel, physical trainers, coaches, commanding officers, etc.), a computing device distinct and remote from the CCU, a tablet, a mobile computing device (e.g., a smart phone), a remote control, etc. For example, the user interface 749 can include a display 758 or one or more inputs 760. The display 758 can be configured to display or otherwise convey (e.g., via speakers or haptic output such as vibration) information to the entity. The inputs 760 can enable the entity to communicate with the CCU 754. The inputs 760 can include a mouse, a keyboard, a USB port, a touchscreen, a microphone, etc. As such, the inputs 760 enable the entity to provide one or more operational instructions or programs to the CCU 754 that can be stored on the memory storage medium 742.

In an embodiment, the user interface 749 is configured to inform the entity about the system 700*b*. For example, the user interface 749 can provide to the entity information about one or more previous impacts. In another example, the user interface 749 can inform the entity that one or more active layers of the system 700*b* have been activated. In another example, the user interface 749 can provide at least one sensing signal to the entity. In another example, the user interface 749 can indicate to the entity the readiness of one or more portions of at least one of the supportive members 750*b*, 750*b'*, 750*b"*. For instance, the user interface 749 can indicate if one or more rigid members 710*b* or other components of at least one of the supportive members 750*b*, 750*b'*, 750*b"* are functioning properly (e.g., needs repair, power source requires charging, etc.).

In an embodiment, the CCU 754 can provide one or more recommendations that an individual wearing at least one of the supportive members 750*b*, 750*b'*, 750*b"* should be removed to a safe location, removed from an athletic event, or medical assistance may be required. The one or more recommendations can be based on whether one or more threshold levels have been met or exceeded as disclosed herein. The CCU 754 can determine that at least one threshold level has been met or exceeded based on the sensing signals received by the CCU 754 from the sensors 720. The sensing signals can include any of the characteristics disclosed herein, such as a force applied to at least one of the supportive members 750*b*, 750*b'*, 750*b"*, a radius of curvature of the impact source, a motion (e.g., speed, direction, location, acceleration, deceleration) of at least one of the supportive members 750*b*, 750*b'*, 750*b"*, one or more sensed characteristics of an individual (e.g., heartrate), etc. In some embodiments, one or more of the supportive members 750*b*, 750*b'*, 750*b"* can be controlled responsive to sensing signals from all of, some of, or only one of the supportive members 750*b*, 750*b'*, 750*b"*. For example, a first supportive member 750*b*, 750*b'*, 750*b"* can includes sensors thereon that detect a potential impact, and responsive thereto, the CCU 754 can cause the inflatable members (not shown) in one or more (e.g., all) of the supportive members 750*b*, 750*b'*, 750*b"* to move the plurality of rigid members associated therewith to move from a first position to a second position effective to protect the individual(s) wearing the supportive member(s) 750*b*, 750*b'*, 750*b"*.

In an embodiment, at least one of the supportive members 750*b*, 750*b'*, 750*b"* can be configured to determine a threshold level and to alert an individual wearing the supportive member 750*b*, 750*b'*, 750*b"* that the threshold level has been met or exceeded. For example, a controller of the supportive member 750*b*, 750*b'*, 750*b"* can include a user interface configured to alert the individual or another entity when a threshold level has been met or exceeded. For example, the device can include a speaker that emits a sound when the threshold level has been met or exceeded. In such an embodiment, the CCU 754 can be omitted.

Figure 8:
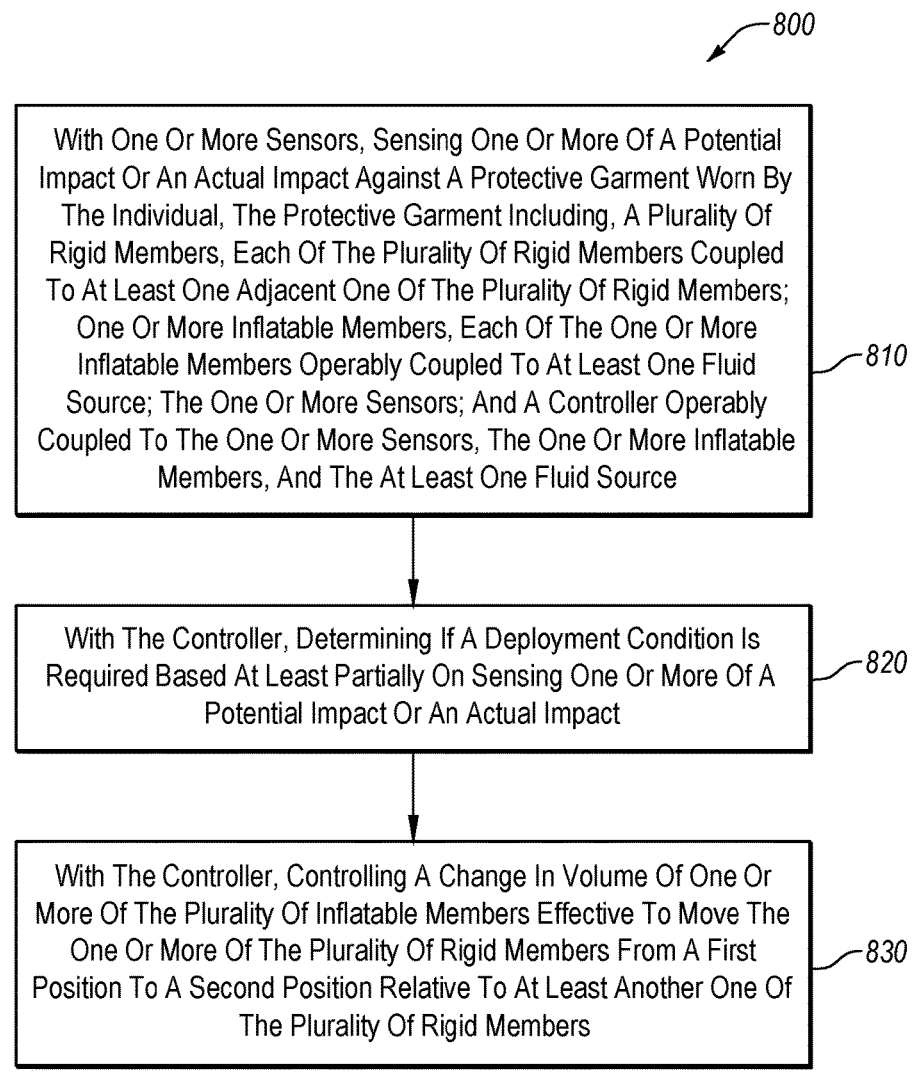
FIG. 8 is a flow chart of a method of protecting one or more body parts of an individual, according to an embodiment.

FIG. 8 is a flow chart of a method 800 of protecting one or more body parts of an individual, according to an embodiment. The method 800 can be carried out using any of the protective garment systems or combinations of components thereof disclosed herein. The method 800 includes an act of 810 sensing one or more of a potential impact or an actual impact against a supportive member worn by the individual with one or more sensors associated with a supportive member. The method 800 includes an act 820 of determining if a deployment condition is required based at least partially on sensing one or more of a potential impact or an actual impact. The act 820 can be carried out by the controller (e.g., or processor therein). The method 800 includes an act 830 of controlling a change in volume of one or more of the plurality of inflatable members effective to move one or more of the plurality of rigid members from a first position to a second position, such as relative to at least another one of the plurality of rigid member. The act 830 can be carried out by the controller (e.g., processor therein) providing one or more directions to one or more of the inflatable members or fluid sources operably coupled thereto. Each of the acts 810-830 are discussed in more detail below.

The act 810 of sensing one or more of a potential impact or an actual impact against a supportive member worn by the individual with one or more sensors associated with a supportive member can include sensing any of the characteristics (e.g., motion, proximity, orientation, etc.) associated with a potential or actual impact disclosed herein. For example, the act 810 of the sensing one or more of potential impact or an actual impact can include sensing one or more of a velocity of an individual or body part thereof, a proximity of the individual or body part thereof to another object, an orientation of the individual or a body part thereof, rotation of the individual or a body part thereof, or pressure applied to the individual or a body part thereof, as sensed at the one or more sensors associated with (e.g., on, in, or adjacent to) the supportive member worn by the individual. The one or more sensors can include any sensors disclosed herein. In an embodiment, at least one of the one or more sensors can be remotely positioned from the individual, such as on an automobile, bicycle, heavy equipment, the ground, or any other position suitable to sense an impact or potential impact to the individual. The act 810 can include transferring one or more sensed characteristics from one or more sensors to the controller.

The one or more sensors can be supported by any supportive member or wearable device disclosed herein. The supportive member used in method 800 can include any of the supportive members disclosed herein. The supportive member can support a plurality of rigid members. Each of the plurality of rigid members coupled to at least one adjacent one of the plurality of rigid members, such as via a linkage. The supportive member can support one or more the plurality of inflatable members, fluid source(s), or at least one controller as disclosed therein.

The act 820 of determining if a deployment condition is required based at least partially on sensing one or more of a potential impact or an actual impact can include determining if the deployment condition is required using the at least one controller (e.g., processor therein). The act 820 of determining if a deployment condition is required can include, with the controller (e.g., processor or memory storage medium), receiving one or more sensed characteristics from the one or more sensors. The act 820 can include with the controller or processor therein, determining if one or more sensed characteristics are indicative of an impact or potential impact.

Determining if the one or more sensed characteristics are indicative of an impact or potential impact can include determining (with the controller or processor therein) if the one or more sensed characteristics are equal to or above a threshold level for the one or more sensed characteristics such as pressure or velocity. For example, determining if a deployment condition is required can include determining, with the processor, if the sensed characteristics of the potential impact or actual impact indicate a force at least equal to a threshold level of the force on the one or more body parts of the individual. Determining if the sensed characteristics of the potential impact or actual impact indicate a characteristic at least equal to a threshold level of the characteristic can include the processor accessing a look-up table of threshold levels stored in the memory storage medium and comparing the sensed characteristic thereto. Such determinations can be made in the millisecond time scale. Determining if the one or more sensed characteristics are equal to or above a threshold level of at least one of a position of the individual, a velocity of the individual, a history of impacts on the individual, a position of a potential impact source, a velocity of a potential impact source, a severity of the an injury, a time of day, an elapsed time, a temperature, or an activity level of the individual. In an embodiment, determining if the sensed characteristics indicate an impact or potential impact can include determining if a velocity and proximity of an object relative to the individual indicate that in impact is taking place or likely to take place. In an embodiment, a threshold level of probability of impact can be assigned in the memory storage medium. For example, responsive to a determined potential impact above a specific probability, the processor can direct the at least one fluid source and one or more inflatable members to change a volume of fluid therein, thereby deploying the one or more rigid members to protect the individual. Suitable probabilities can include 50% likelihood or more, such as about 65% or more, 75%, or more, 80%, or more, or 90% likelihood of impact or more. The probability threshold can be set by the user (e.g., individual, medical professional, parent, etc.).

The act 830 of controlling a change in volume of one or more of the plurality of inflatable members effective to move one or more of the plurality of rigid members from a first position to a second position can be carried out with the controller (e.g., processor). Moving one or more of the plurality of rigid members from a first position to a second position can included moving at least one of the rigid members relative to at least another one of the plurality of rigid member. Moving one or more of the plurality of rigid members from a first position to a second position can include moving one or more of the plurality of rigid members into a deployment position configured to provide greater protection to the individual than in the undeployed position. For example, moving one or more of the plurality of rigid members from a first position to a second position can include moving the plurality of rigid members to reinforce a body part (e.g., joint or limb), provide impact resistance (e.g., at least partially absorb an impact), prevent punctures (e.g., form a shield of an interconnected array of adjacent rigid members), etc.

The act 830 of controlling a change in volume of one or more of the plurality of inflatable members effective to move one or more of the plurality of rigid members can be selective, such as responsive to a sensed actual or potential impact. Such selective control can be based on one or more of a sensed potential or actual impact, location of one or more regions of sensed impacts, the protective garment system history (e.g., past deployments of one or more inflatable members), or the individual's history (e.g., health). Controlling a change in volume of one or more of the plurality of inflatable members can include directing the at least one fluid source or inflatable members associated therewith to alter an amount of fluid in the one or more inflatable members, such as responsive to the determining the deployment condition is required. The processor can be configured to direct the at least one fluid source to alter (e.g., increase or decrease) an amount of fluid in the one or more of the inflatable members. Directing the at least one fluid source to alter an amount of fluid can include directing the at least one fluid source to at least partially fill one or more of the plurality of inflatable members with a fluid, such as a gas, liquid, or foam.

In an embodiment, controlling a change in volume of one or more of the plurality of inflatable members can include controlling a change in volume of only those inflatable members in a region adjacent to the sensors indicating a potential or actual impact. For example, only the inflatable members adjacent to one or more sensors on the abdomen can be selectively controlled responsive to the sensed actual or potential impact at the one or more sensors on the abdomen.

In an embodiment, the method 800 can include causing the plurality of rigid members to return to the first position after controlling the change in volume effective to move the one or more of the plurality of rigid members from a first position to a second position. Causing the plurality of rigid members to return to the first position can include further controlling (with the controller) the volume one or more of the plurality of inflatable members effective to cause the plurality of rigid members to move from the second position to the first position. For example, the method can include resetting the inflatable members, rigid members, and the protective garment system for reuse. Causing the plurality of rigid members to return to the first position can include causing the plurality of inflatable reservoirs to decrease in volume, such as by opening valves to expel fluids therein.

In an embodiment, the method 800 can include placing at least a portion of the protective garment system on the individual. In an embodiment, the method 800 can include inputting one or more instructions, programs, thresholds values, inflation instructions, etc., into the user interface of the protective garment system.

In an embodiment, any of the methods can include or the controllers or sensors can transmit information or data to one or more data storage devices or systems that can be associated with or can include medical records (e.g., medical records of the individual wearing the protective supportive member(s)). For example, the controller can store or transmit data related to the number and severity of impacts received by an individual (e.g., impact force imparted onto the individual, impact energy absorbed by the individual, location(s) of impact(s), etc.). In an embodiment, the medical records of the individual can be associated with or can receive information related to the impact(s) to assess effects of the impact(s) on the health of the individual, to assess whether the individual may need to seek medical attention, etc.

It will be understood that a wide range of hardware, software, firmware, or virtually any combination thereof can be used in the controllers described herein. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more programs running on one or more processors (e.g., as one or more programs running on one or more microprocessors), as firmware, or as virtually any combination thereof. In addition, the reader will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution.

In a general sense, the various embodiments described herein can be implemented, individually and/or collectively, by various types of electro-mechanical systems having a wide range of electrical components such as hardware, software, firmware, or virtually any combination thereof; and a wide range of components that can impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs.

In a general sense, the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). The subject matter described herein can be implemented in an analog or digital fashion or some combination thereof.

The herein described components (e.g., steps), devices, and objects and the discussion accompanying them are used as examples for the sake of conceptual clarity. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

In some instances, one or more components can be referred to herein as "configured to." The reader will recognize that "configured to" or "adapted to" are synonymous and can generally encompass active-state components and/or inactive-state components and/or standby-state components, unless context requires otherwise.

While particular aspects of the present subject matter described herein have been shown and described, it will be apparent that, based upon the teachings herein, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense the convention (e.g., "a system having at least one of A, B, or C" would include but not be limited to systems that have A alone, B alone, C alone, A and B together, A and C together, B and C together, and/or A, B, and C together, etc.). Virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, any recited operations therein can generally be performed in any order. Examples of such alternate orderings can include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, the various aspects and embodiments disclosed herein are for purposes of illustration and are not intended to be limiting, with the true scope and spirit being indicated by the following claims.

What is claimed is:

1. A protective garment system for protecting an individual,
    the protective garment system comprising:
    a plurality of rigid members, each of the plurality of rigid members coupled to at least one adjacent rigid member of the plurality of rigid members;
    at least one fluid source;
    a plurality of inflatable members, each of the plurality of inflatable members operably coupled to the at least one fluid source and associated with at least one of the plurality of rigid members;
    one or more sensors configured to sense at least one of a potential impact or an actual impact of the individual; and
    a controller operably coupled to the one or more sensors and the at least one fluid source,
    wherein:
        at least a first portion of the plurality of rigid members are movable from a first position to a second position;
        each inflatable member of at least a first portion of the plurality of inflatable members is positioned adjacent to one or more rigid members of the first portion of the plurality of rigid members;
        when the inflatable member of the first portion of the plurality of inflatable members inflates, the inflatable member engages the one or more rigid members and moves the one or more rigid members from the first position to the second position; and
        when the one or more rigid members are in the second position, the one or more rigid members interface or partially overlap at least one rigid member of a second portion of the plurality of rigid members.

2. The protective garment system of claim 1, wherein the first position corresponds to an uninflated state and allows for flexibility of one or more portions of a protective garment and the second position corresponds to an inflated state and provides increased rigidity in one or more portions of the protective garment.

3. The protective garment system of claim 1, wherein each of the plurality of inflatable members are operably coupled to the at least one fluid source.

4. The protective garment system of claim 1, wherein the controller is configured to direct the at least one fluid source to controllably supply fluid to the one or more of the plurality of inflatable members in only one or more selected regions of the protective garment system.

5. The protective garment system of claim 1, wherein the first portion of the plurality of rigid members are positioned and configured to at least partially interlock with the second portion of the plurality of rigid members.

6. The protective garment system of claim 1, wherein the one or more sensors are disposed adjacent to the plurality of rigid members and the plurality of inflatable members.

7. The protective garment system of claim 1, wherein the one or more sensors include a sensor array disposed over substantially an entire protective garment.

8. The protective garment system of claim 1, wherein the controller is configured to determine if a deployment condition is required for at least one of the plurality of inflatable members based at least partially on the one or more sensors sensing the at least one of the potential impact or the actual impact of the individual.

9. The protective garment system of claim 1, wherein the controller is configured to direct the at least one fluid source to controllably supply a fluid to one or more of the plurality of inflatable members responsive to receiving an indication of the at least one of the potential impact or the actual impact of the individual from the one or more sensors.

10. The protective garment system of claim 1, wherein:
the one or more sensors are associated with at least one region of the protective garment system; and
the controller is configured to determine if a deployment condition is required for at least one of the plurality of inflatable members in the at least one region based at least partially on the one or more sensors sensing the at least one of the potential impact or the actual impact of the individual.

11. The protective garment system of claim 1, wherein the controller includes a plurality of controllers each of which is operably coupled to at least one of the one or more sensors.

12. The protective garment system of claim 11, wherein each of the plurality of controllers is configured to determine if a deployment condition is required for at least one of the plurality of inflatable members in one or more regions of the protective garment system associated therewith.

13. The protective garment system of claim 1, wherein each of the plurality of rigid members is directly linked to one or more adjacent rigid members of the plurality of rigid members via one or more linkages configured to change from a first linkage state to a second linkage state.

14. The protective garment system of claim 13, wherein the one or more linkages are configured to maintain the one or more adjacent rigid members in the first linkage state prior to inflation of the one or more of the plurality of inflatable members.

15. The protective garment system of claim 13, wherein the one or more linkages include one or more of a resilient material or a fastener.

16. The protective garment system of claim 13, wherein the one or more linkages include a latch that is reversibly separable.

17. The protective garment system of claim 16, wherein the latch is reversibly separable and configured to reconnect responsive to depletion of a fluid in an inflatable reservoir of the one or more of the plurality of inflatable members.

18. The protective garment system of claim 16, wherein the controller is configured to control the latch to reconnect.

19. The protective garment system of claim 16, wherein the latch is configured to remain in the second linkage state after inflation of the one or more of the plurality of inflatable members.

20. The protective garment system of claim 13, wherein the second linkage state is configured to hold the plurality of rigid members in a protective configuration on the individual.

21. The protective garment system of claim 1, wherein at least one fluid source includes:
one or more reactants composed to produce a fluid to at least partially fill an inflatable reservoir of each of the plurality of inflatable members; and
an ignition source configured to cause a reaction between the one or more reactants.

22. The protective garment system of claim 21, wherein:
one or more reactants are stored in separate chemical reservoirs of the at least one fluid source; and
the ignition source includes a mixer configured to mix the one or more reactants.

23. The protective garment system of claim 21, wherein:
the one or more reactants are stored in a single chemical reservoir; and
the ignition source is configured to initiate the reaction between the one or more reactants.

24. The protective garment system of claim 21, wherein:
the one or more reactants are stored in one or more chemical reservoirs of the at least one fluid source; and
the one or more chemical reservoirs are configured to release one or more metered doses of the one or more reactants responsive to direction from the controller.

25. The protective garment system of claim 21, wherein the one or more reactants are stored in a plurality of chemical reservoirs of the at least one fluid source, and wherein each of the plurality of chemical reservoirs is configured to supply a single dose of the one or more reactants responsive to direction from the controller.

26. The protective garment system of claim 25, wherein each of the plurality of chemical reservoirs is configured to sequentially supply a single dose of the one or more reactants responsive to one or more signals from the controller.

27. The protective garment system of claim 1, wherein the at least one fluid source includes a supply of fluid stored in a reservoir.

28. The protective garment system of claim 1, wherein the one or more sensors include one or more of an accelerometer, a proximity sensor, a force sensor, or a pressure sensor.

29. The protective garment system of claim 1, wherein the one or more sensors are configured to sense one or more of deceleration of at least a portion of the individual, a pressure applied to a portion of the individual or a protective garment worn by the individual by an object, a radius of curvature of an object contacting the protective garment system, a predicted force on a body part of the individual, or a direction of likely impact of at least one body part of the individual.

30. The protective garment system of claim 1, wherein the controller is configured to selectively direct the at least one fluid source to supply a fluid into the one or more of the plurality of inflatable members.

31. The protective garment system of claim 1, wherein the controller is configured to selectively direct at least one fluid source in one or more regions of the protective garment system to supply a fluid into the one or more inflatable members in the one or more regions responsive to the at least one of the potential impact or actual impact of the individual sensed by the one or more sensors.

32. The protective garment system of claim 31, wherein the one or more regions include only those regions determined by the controller to be likely to undergo an actual impact.

33. The protective garment system of claim 1, wherein the plurality of rigid members and the plurality of inflatable members form part of one or more of apparel, sportswear, sports equipment, or safety equipment.

34. The protective garment system of claim 1, wherein the controller includes:
a processor; and
memory operably coupled to and accessible by the processor.

35. The protective garment system of claim 33, wherein the memory is configured to store information including one or more of previous impacts against the individual, a deployment history of the plurality of inflatable members, one or more sensed motion characteristics of the individual, a readiness status of one or more portions of the protective garment, program instructions, or threshold levels of force applied to the individual.

36. The protective garment system of claim 35, wherein the controller includes an interface configured to communicate with one or more of a user, a computer, a tablet, a mobile computing device, or a remote control.

37. The protective garment system of claim 36, wherein the interface includes a user interface configured to inform a user or the individual of one or more of previous impacts against the individual, a deployment history of the plurality of inflatable members, sensed motion characteristics, a readiness status of one or more portions of the protective garment system, program instructions, or threshold levels of force applied to the individual.

38. The protective garment system of claim 36, wherein the interface is configured to receive input, instructions, or programming from one or more of the individual, the user, the computer, the tablet, the mobile computing device, or the remote control.

39. The protective garment system of claim 35, wherein the processor is configured to determine if one or more sensed motion characteristics of a potential impact or an actual impact are at least equal to a threshold level for the one or more of a potential impact or an actual impact and, responsive thereto, provide one or more activation signals to the at least one fluid source.

40. The protective garment system of claim 39, wherein the threshold level is determined by a differential of sensed motion characteristics of adjacent sensors of the one or more sensors.

41. The protective garment system of claim 39, wherein the threshold level corresponds to a force indicative of a possible puncture that would result from a sharp object, an acceleration or deceleration indicative of a force capable of breaking bone of the individual, or a motion and a direction of motion indicative of a force capable of damaging a body part of the individual.

42. The protective garment system of claim 39, wherein the processor is configured to adjust the threshold level based on one or more of a history of impacts on the individual, speed of at least one body part of the individual, a location of the individual with respect to one or more objects, a position of a potential impact source, a speed of a potential impact source, an elapsed time of use of the protective garment system, a time of day, a temperature, or an activity level of the individual.

43. The protective garment system of claim 1, wherein the plurality of rigid members are molded to conform to body region of the individual when in one or more of the first position, the second position, or an intermediate position therebetween.

44. The protective garment system of claim 1, wherein:
the second portion of the plurality of rigid members are movable from a first position to a second position;
each inflatable member of at least a second portion of the plurality of inflatable members is positioned adjacent to one or more rigid members of the second portion of the plurality of rigid members;
when the inflatable member of the second portion of the plurality of inflatable members inflates, the inflatable member of the second portion of the plurality of inflatable members engages the one or more rigid members of the second portion of the plurality of rigid members and moves the one or more rigid members of the second portion of the plurality of rigid members from the first position to the second position; and
when the one or more rigid members of the second portion of the plurality of rigid members are in the second position, the one or more rigid members of the second portion of the plurality of rigid members interface or partially overlap at least one rigid member of the first portion of the plurality of rigid members.

45. The protective garment system of claim 44, wherein:
each of the one or more rigid members of the first portion of the plurality of rigid members includes a first end and a second end distal to the first end, each inflatable member of the first portion of the plurality of inflatable members being positioned adjacent the first end of the one or more rigid members of the first portion of the plurality of rigid members;
each of the one or more rigid members of the second portion of the plurality of rigid members includes a first end and a second end distal to the first end of the one or more rigid members of the second portion of the plurality of rigid members, each inflatable member of the second portion of the plurality of inflatable members being positioned adjacent the first end of the one or more rigid members of the second portion of the plurality of rigid members;
when the first portion of the plurality of rigid members and the second portion of the plurality of rigid members are in the second position, a gap is formed between the second end of each of the first portion of the plurality of rigid members and the first end of the second portion of the plurality of rigid members; and
when the first portion of the plurality of rigid members and the second portion of the plurality of rigid members are in the second position, the second end of each of the first portion of the plurality of rigid members interfaces or partially overlaps with the second end of the second portion of the plurality of rigid members.

46. The protective garment system of claim 1, wherein:
the second portion of the plurality of rigid members are movable from a first position to a second position;
at least a third portion of the plurality of rigid members are movable from a first position to a second position;
each inflatable member of at least an additional portion of the plurality of inflatable members is positioned adjacent to one or more rigid members of the third portion of the plurality of rigid members;
one or more rigid members of the second portion of the plurality of rigid members are positioned between the one or more rigid members of the third portion of the plurality of rigid members and the one or more rigid members of the first portion of the plurality of rigid members;
when the inflatable member of the additional portion of the plurality of inflatable members inflates, the inflatable member of the additional portion of the plurality of inflatable members engages the one or more rigid members of the third portion of the plurality of rigid members and moves the one or more rigid members of the third portion of the plurality of rigid members from the first position to the second position; and when the one or more rigid members of the first portion, the second portion, and the third portion of the plurality of rigid members are in the second position, the one or more rigid members of the third portion of the plurality of rigid members interface or partially overlap at least one rigid member of the one or more rigid members of the second portion of the plurality of rigid members.

47. The protective garment system of claim 1, wherein:

the first portion of the plurality of rigid members are rotatably movable from the first position to the second position;

the second portion of the plurality of rigid members are rotatably movable from a first position to a second position;

each inflatable member of at least a second portion of the plurality of inflatable members is positioned adjacent to one or more rigid members of the second portion of the plurality of rigid members;

when the inflatable member of the first portion of the plurality of inflatable members inflates, the inflatable member engages the one or more rigid members of the first portion of the plurality of rigid members and rotates the one or more rigid members of the first portion of the plurality of rigid members from the first position to the second position to interface or partially overlap with the one or more rigid members of the second portion of the plurality of rigid members; and when the inflatable member of the second portion of the plurality of inflatable members inflates, the inflatable member engages the one or more rigid members of the second portion of the plurality of rigid members and rotates the one or more rigid members of the second portion of the plurality of rigid members from the first position to the second position to interface or partially overlap with the one or more rigid members of the first portion of the plurality of rigid members.

48. A protective garment system for protecting one or more body parts of at least one individual, the protective garment system comprising:

at least one supportive member configured to contact one or more body regions of the at least one individual;

a plurality of rigid members at least partially supported by the at least one supportive member, each of the plurality of rigid members coupled to at least one adjacent rigid member of the plurality of rigid members;

at least one fluid source;

a plurality of inflatable members each of which includes an inflatable reservoir, each of the plurality of inflatable members operably coupled to the at least one fluid source;

one or more sensors configured to sense at least one of a potential impact or an actual impact of the individual;

a controller operably coupled to the one or more sensors and the at least one fluid source, the controller configured to, receive sensing signals from the one or more sensors;

determine if the one or more sensing signals are indicative of a potential impact or an actual impact to the individual; and responsive thereto, direct the at least one fluid source to supply a fluid to the one or more inflatable members effective to alter a volume of the inflatable reservoir therein to cause the plurality of rigid members to move from a first position to a second position, wherein:

each inflatable member of at least a first portion of the plurality of inflatable members is positioned adjacent to one or more rigid members of a first portion of the plurality of rigid members;

when the inflatable member of the first portion of the plurality of inflatable members inflates, the inflatable member engages the one or more rigid members and moves the one or more rigid members from the first position to the second position; and when the one or more rigid members are in the second position, the one or more rigid members interface or partially overlap at least one rigid member of a second portion of the plurality of rigid members.

* * * * *